(12) United States Patent
Ma

(10) Patent No.: US 11,491,347 B2
(45) Date of Patent: Nov. 8, 2022

(54) SYSTEMS AND METHODS FOR DRIVING LEAVES OF A MULTI-LEAF COLLIMATOR

(71) Applicant: SHANGHAI UNITED IMAGING HEALTHCARE CO., LTD., Shanghai (CN)

(72) Inventor: Boqi Ma, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/105,551

(22) Filed: Nov. 26, 2020

(65) Prior Publication Data

US 2021/0283424 A1    Sep. 16, 2021

Related U.S. Application Data

(63) Continuation of application No. PCT/CN2020/079013, filed on Mar. 12, 2020.

(51) Int. Cl.
*A61N 5/10* (2006.01)

(52) U.S. Cl.
CPC ......... *A61N 5/1045* (2013.01); *A61N 5/1065* (2013.01); *A61N 2005/1074* (2013.01)

(58) Field of Classification Search
CPC ............... A61N 5/1045; A61N 5/1065; A61N 2005/1074; A61N 5/1048; A61N 5/1077
See application file for complete search history.

(56) References Cited

U.S. PATENT DOCUMENTS

| 8,637,841 | B2 * | 1/2014 | Prince ................. A61N 5/1045 250/505.1 |
| 10,518,110 | B1 * | 12/2019 | Jimenez-Carvajal ........................ G21K 1/046 |
| 2004/0184578 | A1 | 9/2004 | Nakano |
| 2009/0041188 | A1 * | 2/2009 | Keall ................... A61N 5/1042 378/65 |
| 2014/0239204 | A1 | 8/2014 | Orton et al. |

(Continued)

FOREIGN PATENT DOCUMENTS

| CN | 102755696 A | 10/2012 |
| CN | 103845816 A | 6/2014 |

(Continued)

OTHER PUBLICATIONS

International Search Report in PCT/CN2020/079013 dated Dec. 16, 2020, 4 pages.

(Continued)

*Primary Examiner* — Marcus H Taningco
(74) *Attorney, Agent, or Firm* — Metis IP LLC

(57) ABSTRACT

A method for driving a leaf of a multi-leaf collimator (MLC) is provided. The method may include obtaining a target position of the leaf; identifying a current position of the leaf; generating a first control signal based on the target position of the leaf and the current position of the leaf; generating a second control signal based on at least one of a target velocity of the leaf, a target acceleration of the leaf, or a current angle of the leaf; generating a third control signal based on the first control signal and the second control signal; and/or causing a drive circuit to generate a driving signal for driving the leaf to move towards the target position by providing the third control signal to the drive circuit.

19 Claims, 11 Drawing Sheets

(56) References Cited

U.S. PATENT DOCUMENTS

| | | | |
|---|---|---|---|
| 2017/0354393 | A1 | 12/2017 | Bose et al. |
| 2020/0016430 | A1* | 1/2020 | Yang .................. G21K 1/046 |
| 2020/0061390 | A1 | 2/2020 | Ma et al. |
| 2021/0228908 | A1* | 7/2021 | Stahl .................. A61N 5/1036 |

FOREIGN PATENT DOCUMENTS

| | | |
|---|---|---|
| CN | 203896236 U | 10/2014 |
| CN | 105467899 A | 4/2016 |
| CN | 105999567 A | 10/2016 |
| CN | 106512221 A | 3/2017 |
| CN | 108628174 A | 10/2018 |
| CN | 108785877 A | 11/2018 |
| JP | 2010005149 A * | 1/2010 |

OTHER PUBLICATIONS

Written Opinion in PCT/CN2020/079013 dated Dec. 16, 2020, 5 pages.
First Office Action in Chinese Application No. 202080003818.2 dated Jun. 2, 2022, 14 pages.

* cited by examiner

SYSTEMS AND METHODS FOR DRIVING LEAVES OF A MULTI-LEAF COLLIMATOR

CROSS-REFERENCE TO RELATED APPLICATIONS

This present application is a continuation of International Application No. PCT/CN2020/079013, filed on Mar. 12, 2020, the contents of which are hereby incorporated by reference.

TECHNICAL FIELD

The present disclosure generally relates to a multi-leaf collimator, and more particularly to systems and methods for driving leaves of a multi-leaf collimator.

BACKGROUND

Radiotherapy has been widely employed in cancer treatment in which ionizing radiation (e.g., X-rays) is guided towards a treatment region (e.g., a tumor). Radiotherapy can bring about an alleviation of an object's symptom. Generally, it is desirable to delimit the radiation rays so that the radiation dose is maximized in the treatment region and minimized in the healthy tissue of the object. A multi-leaf collimator (MLC) plays an important role in delimiting the radiation rays. An MLC can have a plurality of leaf pairs, and the leaves can be generally driven by driving motors (e.g., through a closed-loop control system), which can offer a relatively high spatial resolution and precision. However, one or more motion factors (e.g., gravity, friction, acceleration, deceleration, or the like) associated with the leaves within the treatment process can affect the motion of the leaves, thereby introducing movement lags of the leaves, and/or reducing control precision of the control system. Therefore, it is desirable that a compensation is provided for the motion control of the leaves of the MLC to improve control precision.

SUMMARY

In one aspect of the present disclosure, a method for driving a leaf of a multi-leaf collimator (MLC) is provided. The method may be implemented on a machine including at least a processor and a storage device. The method may include: obtaining a target position of the leaf; identifying a current position of the leaf; generating a first control signal based on the target position of the leaf and the current position of the leaf; generating a second control signal based on at least one of a target velocity of the leaf, a target acceleration of the leaf, or a current angle of the leaf; generating a third control signal based on the first control signal and the second control signal; and/or causing a drive circuit to generate a driving signal for driving the leaf to move towards the target position by providing the third control signal to the drive circuit.

In some embodiments, the generating a second control signal based on at least one of a target velocity of the leaf, a target acceleration of the leaf, or a current angle of the leaf may include: obtaining the target acceleration of the leaf; and/or generating a first component of the second control signal based on the target acceleration of the leaf and a first gain.

In some embodiments, the generating a first component of the second control signal based on the target acceleration of the leaf and a first gain may include: generating the first component of the second control signal by multiplying the target acceleration of the leaf by the first gain.

In some embodiments, the first gain may relate to a mass of the leaf and a characteristic of the drive circuit.

In some embodiments, the MLC may be mounted on a gantry, and the first gain may be determined according to a process including: positioning the gantry at an initial angle of 0°; detecting a plurality of velocity curves by driving the leaf to move from a stationary state under a plurality of fourth control signals; generating, based on the plurality of velocity curves, an acceleration curve illustrating a relation between a plurality of accelerations and the plurality of fourth control signals; and/or designating a slope of the acceleration curve as the first gain.

In some embodiments, the generating a second control signal based on at least one of a target velocity of the leaf, a target acceleration of the leaf, or a current angle of the leaf may include: obtaining the target velocity of the leaf and the current angle of the leaf; and/or generating a second component of the second control signal based on the target velocity of the leaf, the current angle of the leaf, and at least one of a second gain, a third gain, or a fourth gain.

In some embodiments, the generating a second component of the second control signal may include: determining a first product of a cosine of the current angle of the leaf multiplied by the second gain; determining a second product of a sine of the current angle of the leaf multiplied by the third gain; determining a sum of the first product and the second product; adjusting the sum according to a direction of the target velocity of the leaf; determining a third product of the target velocity of the leaf multiplied by the fourth gain; and/or generating the second component of the second control signal based on the sum and the third product.

In some embodiments, the MLC may be mounted on a gantry, and the second gain may be determined according to a process including: positioning the gantry at an initial angle of 0°; driving the leaf to move from a stationary state by increasing, from 0 to a critical value, a fourth control signal, in which the leaf starts to move under the fourth control signal with the critical value; and/or determining the second gain based on the critical value.

In some embodiments, the MLC may be mounted on a collimator, the collimator is mounted on a gantry, and the third gain may be determined according to a process including: positioning the gantry at an angle of 90°; positioning the collimator at an initial angle of 0°; driving the leaf to move upwards from a stationary state by increasing, from 0 to a first critical value, a fourth control signal, in which the leaf starts to move upwards under the fourth control signal with the first critical value; driving the leaf to move downwards from a stationary state by increasing, from 0 to a second critical value, a fourth control signal, in which the leaf starts to move downwards under the fourth control signal with the second critical value; and/or determining the third gain based on a difference between the first critical value and the second critical value.

In some embodiments, the MLC may be mounted on a gantry, and the fourth gain may be determined according to a process including: positioning the gantry at an initial angle of 0°; detecting a plurality of velocities of the leaf in a steady-state motion under a plurality of fourth control signals; generating a velocity curve illustrating a relation between the plurality of velocities and the plurality of fourth control signals; and/or designating a slope of the velocity curve as the fourth gain.

In some embodiments, the generating a second control signal based on at least one of a target velocity of the leaf, a target acceleration of the leaf, or a current angle of the leaf may include: obtaining the current angle of the leaf; and/or generating, based on the current angle of the leaf and a fifth gain, a third component of the second control signal.

In some embodiments, the generating, based on the current angle of the leaf and a fifth gain, a third component of the second control signal may include: generating the third component of the second control signal by multiplying a sine of the current angle of the leaf by the fifth gain.

In some embodiments, the MLC may be mounted on a collimator, the collimator is mounted on a gantry, and the fifth gain may be determined according to a process including: positioning the gantry at an angle of 90°; positioning the collimator at an initial angle of 0°; driving the leaf to move upwards from a stationary state by increasing, from 0 to a first critical value, a fourth control signal, in which the leaf starts to move upwards under the fourth control signal with the first critical value; driving the leaf to move downwards from a stationary state by increasing, from 0 to a second critical value, a fourth control signal, in which the leaf starts to move downwards under the fourth control signal with the second critical value; and/or determining the third gain based on a sum of the first critical value and the second critical value.

In some embodiments, the generating a first control signal based on the target position of the leaf and the current position of the leaf may include: determining a first difference between the target position of the leaf and the current position of the leaf; generating an output signal of a position control loop by inputting the first difference to the position control loop; identifying a current velocity of the leaf; determining a second difference between the output signal of the position control loop and the current velocity of the leaf; and/or generating the first control signal based on the second difference and a velocity control loop.

In some embodiments, the identifying a current velocity of the leaf may include: detecting the current velocity of the leaf using a displacement sensor or an encoder.

In some embodiments, the identifying a current position of the leaf may include: detecting the current position of the leaf using a displacement sensor or an encoder.

In some embodiments, the MLC may be mounted on a collimator, the collimator may be mounted on a gantry, and the method may further include: determining the current angle of the leaf based on a current angle of the collimator and a current angle of the gantry.

In some embodiments, the third control signal may be a pulse width modulation (PWM) signal.

In another aspect of the present disclosure, a system for driving a leaf of a multi-leaf collimator (MLC) is provided. The system may include at least one storage device storing a set of instructions; and at least one processor in communication with the storage device. When executing the set of instructions, the at least one processor may be configured to cause the system to perform operations including: obtaining a target position of the leaf; identifying a current position of the leaf; generating a first control signal based on the target position of the leaf and the current position of the leaf; generating a second control signal based on at least one of a target velocity of the leaf, a target acceleration of the leaf, or a current angle of the leaf; generating a third control signal based on the first control signal and the second control signal; and/or causing a drive circuit to generate a driving signal for driving the leaf to move towards the target position by providing the third control signal to the drive circuit.

In another aspect of the present disclosure, a non-transitory computer readable medium is provided. The non-transitory computer readable medium may include at least one set of instructions for driving a leaf of a multi-leaf collimator (MLC). When executed by one or more processors of a computing device, the at least one set of instructions may cause the computing device to perform a method, including: obtaining a target position of the leaf; identifying a current position of the leaf; generating a first control signal based on the target position of the leaf and the current position of the leaf; generating a second control signal based on at least one of a target velocity of the leaf, a target acceleration of the leaf, or a current angle of the leaf; generating a third control signal based on the first control signal and the second control signal; and/or causing a drive circuit to generate a driving signal for driving the leaf to move towards the target position by providing the third control signal to the drive circuit.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
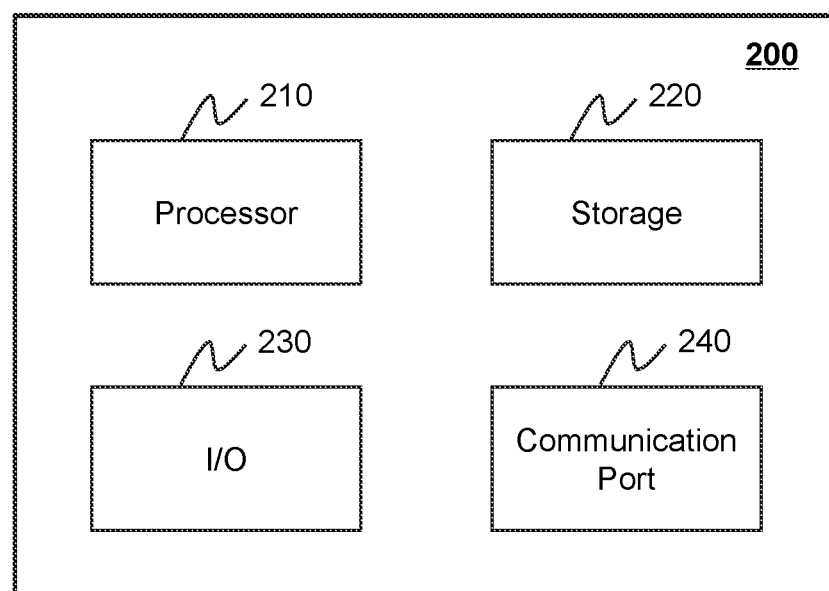
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in inverted order, or simultaneously. Moreover, one or more other operations may be added to the flowcharts. One or more operations may be removed from the flowcharts.

The present disclosure relates to systems and methods for driving one or more leaves of a multi-leaf collimator (MLC). Because of the existence of one or more motion factors (e.g., gravity, friction, acceleration, deceleration, or the like), a conventional closed-loop feedback control of the leaves of the MLC may introduce movement lags of the leaves, thereby reducing control precision of the control system. For example, if the velocity of a leaf speeds up or slows down frequently during the treatment process, acceleration lags may be induced when using only the feedback control. Because of the acceleration lags, the leaf can't move at a desired acceleration in time, thereby inducing a relatively large error. As another example, if a leaf of the MLC or the MLC starts to move from a static state, there may be friction(s) (e.g., a slide friction, a viscous friction, or the like) impeding the movement of the leaf or the MLC. The viscous friction may relate to a speed of a leaf. Because an initial driving force output by a driving device of the MLC is generally less than the friction(s) when using only the feedback control, the leaf or the MLC may remain static for a certain period of time in the initial stage of driving, and thus, the position lags and velocity lags may be induced. One reason for the initial driving force less than the friction(s) is that a position error (between a desired position and a current position) and/or a velocity error (between a desired velocity and a current velocity) exist when using only the feedback control. As a further example, the gravity of the leaves of the MLC may be varied when the MLC rotates with a gantry of a radiation delivery device, thereby reducing the dynamic following accuracy of the feedback control.

In the present disclosure, a feedforward control may be combined with the closed-loop feedback control, and a feedforward compensation can be introduced into the closed-loop feedback control, thereby reducing or eliminating movement lags of the leaves. The feedforward control may generate one or more control signals associated with the motion factors (e.g., gravity, frictions, acceleration or deceleration, or the like) based on predetermined target velocities, predetermined target accelerations, and/or current angles of the leaves. The control signals may be used to reduce or eliminate the effect of the motion factors in the motion of the leaves. The systems and methods in the present disclosure can combine the advantages of the feedback control and those of feedforward control, and improve the control precision of the control system. Specifically, in some embodiments, the systems and methods in the present disclosure may obtain a target position of a leaf, identify a current position of the leaf, generate a first control signal based on the target position of the leaf and the current position of the leaf, generate a second control signal based on at least one of a target velocity of the leaf, a target acceleration of the leaf, and a current angle of the leaf, generate a third control signal based on the first control signal and the second control signal, and cause a drive circuit to generate a driving signal for driving the leaf to move towards the target position by providing the third control signal to the drive circuit.

Figure 1:
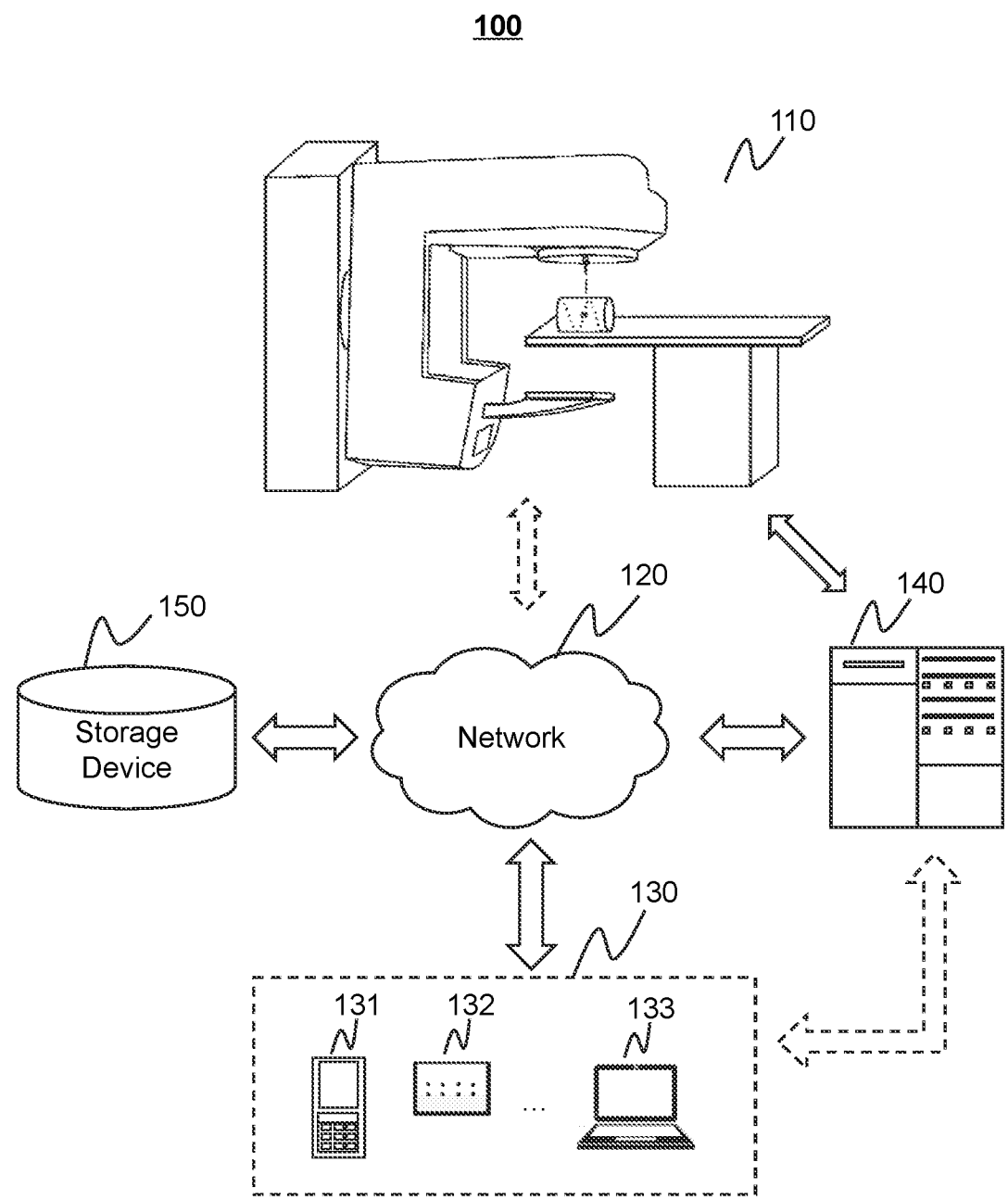
FIG. 1 is a schematic diagram illustrating an exemplary radiotherapy system according to some embodiments of the present disclosure.

FIG. 1 is a schematic diagram illustrating an exemplary radiotherapy system according to some embodiments of the present disclosure. As shown in FIG. 1, the radiotherapy system 100 may include a radiation delivery device 110, a network 120, one or more terminals 130, a processing device 140, and a storage device 150. In some embodiments, the terminal(s) 130 may be used as upper computer(s) (or host computer(s)), while the processing device 140 may be used as a lower computer (or a slave computer). The components in the radiotherapy system 100 may be connected in one or more of various ways. Merely by way of example, the radiation delivery device 110 may be connected to the processing device 140 directly (e.g., via optical fiber (e.g., a peripheral component interconnect express (PCI-E) cable)). As another example, the radiation delivery device 110 may be connected to the processing device 140 through the network 120 as indicated by the bi-directional arrow in dotted lines linking the radiation delivery device 110 and the network 120. As still another example, the storage device 150 may be connected to the processing device 140 directly or through the network 120. As still another example, the terminal 130 may be connected to the processing device 140 directly (as indicated by the bi-directional arrow in dotted lines linking the terminal 130 and the processing device 140) or through the network 120.

In some embodiments, the radiation delivery device 110 may be a radiotherapy (RT) device. In some embodiments, the RT device may deliver one or more radiation beams to a treatment region (e.g., a tumor) of an object (e.g., a patient) for causing an alleviation of the object's symptom. In some embodiments, the RT device may include a linear accelerator (also referred to as "linac"). The linac may generate and emit a radiation beam (e.g., an X-ray beam) from a treatment head. The radiation beam may pass through one or more collimators (e.g., an MLC)) forming certain shapes, and enter into the object. In some embodiments, the radiation beam may include electrons, photons, or other types of radiation. In some embodiments, the energy of the radiation beam may be in the megavoltage range (e.g., >1 MeV), and may therefore be referred to as a megavoltage beam. The treatment head may be coupled to a gantry. The gantry may rotate, for example, clockwise or counter-clockwise around a gantry rotation axis. In some embodiments, the treatment head may rotate along with the gantry. In some embodiments, the RT device may further include a table configured to support the object during radiation treatment.

In some embodiments, the radiation delivery device 110 may further include one or more MLCs (not shown in FIG. 1). The MLC(s) may be configured to collimate radiation beam(s) of the radiation delivery device 110 and/or define the beam shape(s) thereof. In some embodiments, the MLC may include a plurality of leaves. The plurality of leaves may form an aperture. The aperture may define or modify the shape of the beam. In some embodiments, one or more leaves of the MLC may be moved according to a treatment plan. In some embodiments, the shape of the aperture may be changed according to a desired segment shape of the treatment plan.

In some embodiments, the radiation delivery device 110 may further include one or more driving circuits (not shown in FIG. 1). In some embodiments, the driving circuit may generate driving signal(s) to drive the leaves of the MLC to move towards target position(s) during treatment. In some embodiments, the driving circuits may be set in the radiation delivery device 110, and may communicate with the processing device 140 via the connection between the radiation delivery device 110 and the processing device 140. For example, the processing device 140 may provide (or send) a control signal to the drive circuit, and accordingly, the drive circuit may generate a driving signal for driving the leaves to move towards the target position(s).

In some embodiments, the radiation delivery device 110 may further include one or more actuators configured to actuate the leaves to move. In some embodiments, each leaf may be actuated by an actuator. Exemplary actuators may include motors, compressed gas loaded in one or more cylinders, etc. In the following descriptions, motors are described for illustration purposes, and it should be noted that any other type of actuators can be used to actuate the leaves to move when using the driving methods and systems of the present disclosure.

In some embodiments, the radiation delivery device 110 may further include one or more position detection devices (not shown in FIG. 1). A position detection device may be configured to detect a current position of a leaf, and/or a current velocity of the leaf directly or indirectly. In some embodiments, the position detection device may detect a displacement of the leaf, and the current position of the leaf may be determined based on the displacement of the leaf and an initial position of the leaf, and accordingly, the current velocity of the leaf may be determined based on the displacement of the leaf and a time for the leaf movement. Exemplary position detection device(s) may include a magnetic displacement sensor (e.g., a Hall effect sensor), a grating displacement sensor, an encoder (e.g., an encoder mounted on an actuator (e.g., a motor, a cylinder, or the like)), a potentiometer (e.g., a potentiometer mounted on a motor), or the like, or any combination thereof. In some embodiments, a leaf may have a corresponding position detection device.

Merely by way of example, a magnetic displacement sensor may be used to detect the current position and/or current velocity of a leaf. The magnetic displacement sensor may include a magnetic element, and/or a magnetic sensor corresponding to the magnetic element. In some embodiments, the magnetic element may include a bar magnet. In some embodiments, the magnetic sensor may include a Hall effect sensor. In some embodiments, the magnetic element may be set on the leaf, while the magnetic sensor may be set on a housing (see FIGS. 9-10) of the MLC. Alternatively, the magnetic sensor may be set on the leaf, while the magnetic element may be set on the housing of the MLC. If the magnetic element moves with the leaf and relative to the magnetic sensor, a magnetic field sensed by the magnetic sensor may be varied, and a pulse signal may be output by the magnetic sensor. In some embodiments, a displacement of the leaf may be determined based on the number (or count) of pulses output by the Hall effect sensor, and accordingly, the position and/or velocity of the leaf may be determined as illustrated above.

As another example, an encoder may be used to detect the current position and/or current velocity of a leaf. In some embodiments, the encoder may be mounted on the actuator (e.g., the motor), and detect a number (or count) of revolutions of the actuator. The displacement of the leaf may be determined based on the number (or count) of revolutions of the actuator, and accordingly, the position and/or velocity of the leaf may be determined as illustrated above.

As a further example, a potentiometer may be used to detect the current position and/or current velocity of a leaf. In some embodiments, the potentiometer may be mounted on the actuator (e.g., the motor). If the actuator actuates the leaf to move, the potentiometer may output a resistance or voltage signal corresponding to the displacement of the leaf. The displacement of the leaf may be determined based on the resistance output by the potentiometer, and accordingly, the position and/or velocity of the leaf may be determined as illustrated above.

In some embodiments, a leaf may have two corresponding position detection devices. For example, the leaf may have a magnetic displacement sensor and a potentiometer. The displacements of the leaf detected by the two position detection devices may be used to determine whether a position feedback relating to the detected position is abnormal (i.e., whether an encoder is abnormal).

In some embodiments, the current position of the leaf and/or the current velocity of the leaf may be transmitted to the processing device 140 (e.g., the control signal generation module 406) to generate control signal(s). In some embodiments, the current position of the leaf may be used as a position feedback signal input into a position control loop (e.g., the position loop 808 in FIG. 8). In some embodiments, the current velocity of the leaf may be used as a velocity feedback signal input into a velocity control loop (e.g., the velocity loop 810 in FIG. 8). More descriptions of the generation of the control signal(s) may be found elsewhere in the present disclosure (e.g., FIG. 8 and descriptions thereof). In some embodiments, the current position of the leaf and/or the current velocity of the leaf may be further transmitted to the terminal(s) 130 for display.

In some embodiments, the object to be treated or scanned (also referred to as imaged) may include a body, substance, or the like, or any combination thereof. In some embodiments, the object may include a specific portion of a body, such as a head, a thorax, an abdomen, or the like, or any combination thereof. In some embodiments, the object may include a specific organ, such as a breast, an esophagus, a trachea, a bronchus, a stomach, a gallbladder, a small intestine, a colon, a bladder, a ureter, a uterus, a fallopian tube, etc.

The network 120 may include any suitable network that can facilitate exchange of information and/or data for the radiotherapy system 100. In some embodiments, one or more components of the radiotherapy system 100 (e.g., the radiation delivery device 110, the terminal(s) 130, the processing device 140, the storage device 150, etc.) may communicate information and/or data with one or more other components of the radiotherapy system 100 via the network 120. For example, the processing device 140 may obtain user instructions from the terminal(s) 130 via the network 120. In some embodiments, a control device of the MLC and a lower computer may be connected via a peripheral component interconnect express (PCI-E) cable. In some embodiments, the processing device 140 may be used as the lower computer, and the processing device 140 may obtain data corresponding to the leaves of the MLC directly via the PCI-E cable. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiotherapy system 100 may be connected to the network 120 to exchange data and/or information.

Figure 3:
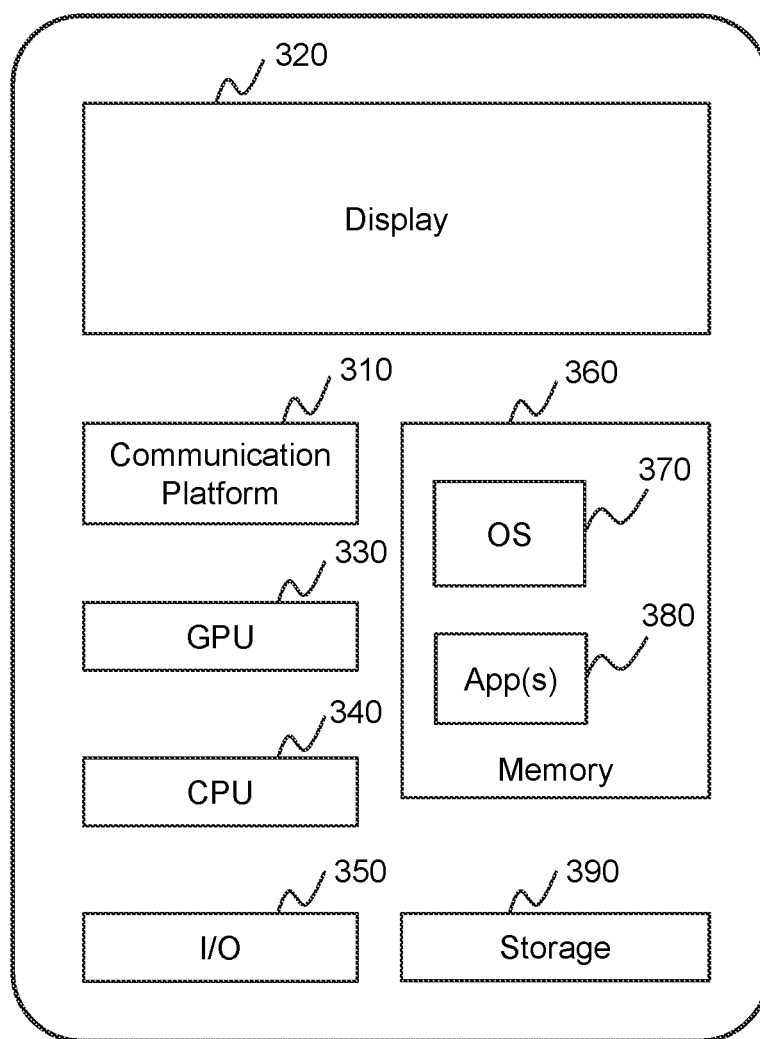
FIG. 3 is a schematic diagram illustrating exemplary hardware and/or software components of an exemplary mobile device 300 on which the terminal may be implemented according to some embodiments of the present disclosure.

The terminal(s) 130 may enable interactions between a user and the radiotherapy system 100. The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140. In some embodiments, the terminal(s) 130 may remotely operate the radiation delivery device 110. In some embodiments, the terminal(s) 130 may operate the radiation delivery device 110 via a wireless connection. In some embodiments, the terminal(s) 130 may receive information and/or instructions inputted by a user, and send the received information and/or instructions to the radiation delivery device 110 or the processing device 140 via the network 120. In some embodiments, the terminal(s) 130 may receive data and/or information from the processing device 140. In some embodiments, the terminal(s) 130 may be part of the processing device 140. In some embodiments, the terminal(s) 130 may be omitted. In some embodiments, the terminal(s) 130 may include a control handle, a control box, a console, etc.

The processing device 140 may process data and/or information obtained from the radiation delivery device 110, the terminal 130, and/or the storage device 150. For example, the processing device 140 may obtain a target position of a leaf. As another example, the processing device 140 may identify a current position of the leaf. As still another example, the processing device 140 may generate a first control signal based on the target position of the leaf and the current position of the leaf. As still another example, the processing device 140 may generate a second control signal based on at least one of a target velocity of the leaf, a target acceleration of the leaf, and a current angle of the leaf. As a further example, the processing device 140 may generate a third control signal based on (e.g., by summing) the first control signal and the second control signal. As still a further example, the processing device 140 may cause a drive circuit to generate a driving signal for driving the leaf to move towards the target position by providing the third control signal to the drive circuit.

In some embodiments, the processing device 140 may be a computer, a user console, a single server or a server group, etc. The server group may be centralized or distributed. In some embodiments, the processing device 140 may be local or remote. For example, the processing device 140 may access information and/or data stored in the radiation delivery device 110, the terminal 130, and/or the storage device 150 via the network 120. As another example, the processing device 140 may be directly connected to the radiation delivery device 110, the terminal 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

In some embodiments, components of the radiotherapy system 100 (e.g., the radiation delivery device 110, the terminal 130, the processing device 140) may communicate with each other in a treatment process. For example, before the treatment process, the terminal 130 may send instruction(s) or information related to target position(s) of a leaf to the processing device 140. The processing device 140 may determine preset velocities and/or preset accelerations based on the target position(s), and/or store the preset velocities and/or preset accelerations. As another example, before the treatment process, the preset velocities and/or preset accelerations may be determined by the terminal 130, and/or stored in the terminal 130.

Alternatively, the terminal 130 may transmit the preset velocities and/or preset accelerations to the processing device 140, and the preset velocities and/or preset accelerations may be stored in the processing device 140. As still another example, during the treatment process, the processing device 140 may obtain the preset velocities and/or preset accelerations from the terminal 130. As a further example, during the treatment process, the radiation delivery device 110 may transmit the current position and/or the current velocity of the leaf to the processing device 140, and the processing device 140 may drive the leaf to move based on the preset velocities, the preset accelerations, the current position, and/or the current velocity. As still a further example, the processing device 140 may transmit the current position and/or the current velocity of the leaf to the terminal 130 for display.

The storage device 150 may store data, instructions, and/or any other information. In some embodiments, the storage device 150 may store data obtained from the radiation delivery device 110, the terminal 130 and/or the processing device 140. For example, the storage device 150 may store a treatment plan, parameters related to a trajectory generation, parameters related to a motion control (e.g., parameters related to the feedback control and/or the feedforward control (e.g., one or more gains of the control system)), parameters related to motion statuses of the leaves (e.g., a gravity, a friction, a velocity, an acceleration, a target position, a current position, etc.), or the like. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the radiotherapy system 100 (e.g., the processing device 140, the terminal 130, etc.). One or more components in the radiotherapy system 100 may access the data or instructions stored in the storage device 150 via the network 120. In some embodiments, the storage device 150 may be directly connected to or communicate with one or more other components in the radiotherapy system 100 (e.g., the processing device 140, the terminal 130, etc.). In some embodiments, the storage device 150 may be part of the processing device 140. In some embodiments, the processing device 140 may be connected to or communicate with the radiation delivery device 110 via the network 120, or at the backend of the processing device 140.

FIG. 2 is a schematic diagram illustrating exemplary hardware and/or software components of an exemplary computing device on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process data obtained from the radiation delivery device 110, the terminal 130, the storage device 150, and/or any other component of the radiotherapy system 100. In some embodiments, the processor 210 may determine preset position(s) of the leaves based on information relating to a treatment plan. The treatment plan may be obtained from a treatment planning system (TPS) associated with the radiotherapy system 100. The information relating to the treatment plan may include preoperative medical image(s) representing the internal anatomical information of an object to be treated or imaged. In some embodiments, the processor 210 may perform trajectory generation based on the preset position(s). In some embodiments, the processor 210 may perform motion control based on the generated trajectory. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the radiation delivery device 110, the terminal 130, the storage device 150, and/or any other component of the radiotherapy system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for driving the leaves of the MLC.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the radiation delivery device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiotherapy system 100 via the network 120. In some embodiments, a user may input parameters to the radiotherapy system 100, via the mobile device 300.

In order to implement various modules, units and their functions described above, a computer hardware platform may be used as hardware platforms of one or more elements (e.g., the processing device 140 and/or other components of the radiotherapy system 100 described in FIG. 1). Since these hardware elements, operating systems and program languages are common; it may be assumed that persons skilled in the art may be familiar with these techniques and they may be able to provide information needed in the imaging according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computing device.

Figure 4:
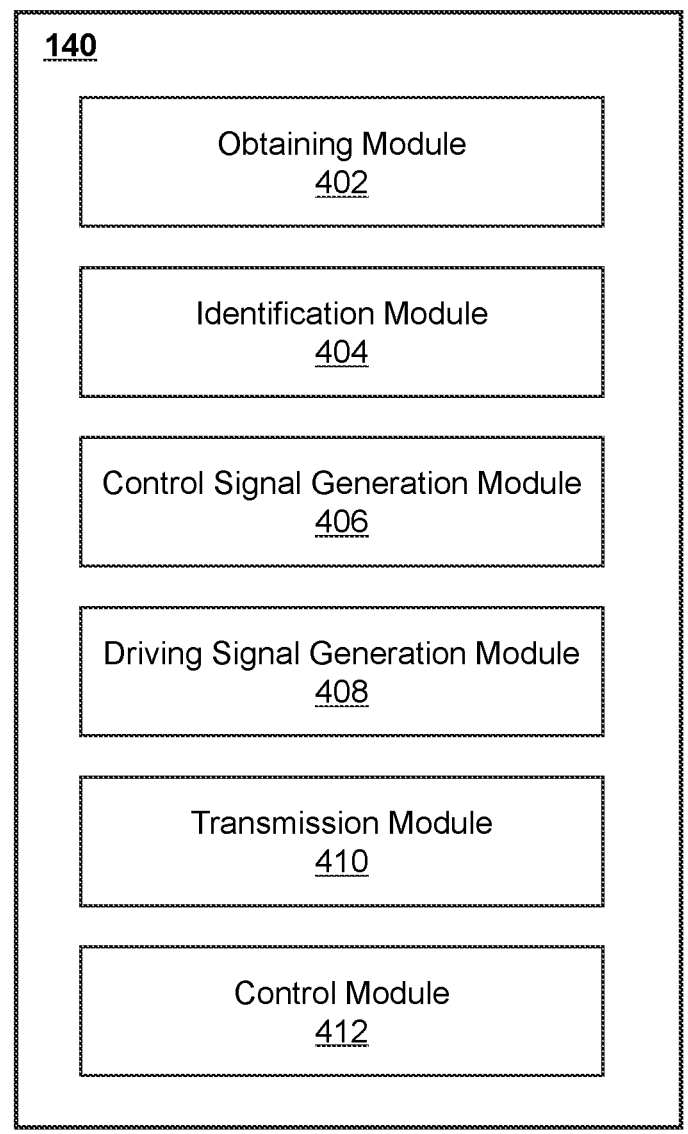
FIG. 4 is a block diagram illustrating an exemplary processing device according to some embodiments of the present disclosure.

FIG. 4 is a block diagram illustrating an exemplary processing device according to some embodiments of the present disclosure. The processing device 140 may include an obtaining module 402, an identification module 404, a control signal generation module 406, a driving signal generation module 408, a transmission module 410, and a control module 412.

The obtaining module 402 may obtain information related to the radiotherapy system 100. For example, the obtaining module 402 may obtain a target position of a leaf. In some embodiments, the target position of the leaf may be obtained from the storage device 150 or an external data source. In some embodiments, the obtaining module 402 may obtain a target acceleration of a leaf, a target velocity of a leaf, a current position of a leaf, a current velocity of a leaf, and/or a current angle of a leaf. More descriptions of the obtaining module 402 may be found elsewhere in the present disclosure (e.g., FIGS. 5 and 7 and descriptions thereof).

The identification module 404 may identify one or more current statuses relating to a leaf. For example, the identification module 404 may identify a current position of the leaf. As another example, the identification module 404 may identify a current velocity of the leaf (see the velocity feedback signal illustrated in FIG. 8). More descriptions of the identification module 404 may be found elsewhere in the present disclosure (e.g., FIGS. 5-6 and descriptions thereof).

The control signal generation module 406 may generate one or more control signals for driving the leaf to move. For example, the control signal generation module 406 may generate a first control signal. As another example, the control signal generation module 406 may generate a second control signal. As a further example, the control signal generation module 406 may generate a third control signal based on the first control signal and/or the second control signal. In some embodiments, the control signal generation module 406 may determine a first difference between the target position of the leaf and the current position of the leaf. In some embodiments, the control signal generation module 406 may generate an output signal of a position control loop by inputting the first difference. In some embodiments, the control signal generation module 406 may determine a second difference between an output signal of the position control loop and the current velocity of the leaf. In some embodiments, the control signal generation module 406 may generate a first component of the second control signal. The first component of the second control signal may be an acceleration feedforward control signal. In some embodiments, the control signal generation module 406 may generate a second component of the second control signal. The second component of the second control signal may be a friction feedforward control signal. In some embodiments, the control signal generation module 406 may generate a third component of the second control signal. The third component of the second control signal may be a gravity feedforward control signal. In some embodiments, the control signal generation module 406 may generate the second control signal based on the first component, the second component, and/or the third component. In some embodiments, the control signal generation module 406 may generate a third control signal (i.e., the compensated control signal). More descriptions of the control signal generation module 406 may be found elsewhere in the present disclosure (e.g., FIGS. 5-8 and descriptions thereof).

The driving signal generation module 408 may cause a drive circuit to generate a driving signal. More descriptions of the driving signal generation module 408 may be found elsewhere in the present disclosure (e.g., operation 512 in FIG. 5 and descriptions thereof).

The transmission module 410 may provide or send the third control signal to the drive circuit. More descriptions of the transmission module 410 may be found elsewhere in the present disclosure (e.g., operation 512 in FIG. 5 and descriptions thereof).

The control module 412 may control a movement of the leaf towards the target position. More descriptions of the control module 412 may be found elsewhere in the present disclosure (e.g., operation 512 in FIG. 5 and descriptions thereof).

It should be noted that the above description of the processing device 140 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the obtaining module 402 and the identification module 404 may be integrated into a single module.

Figure 5:
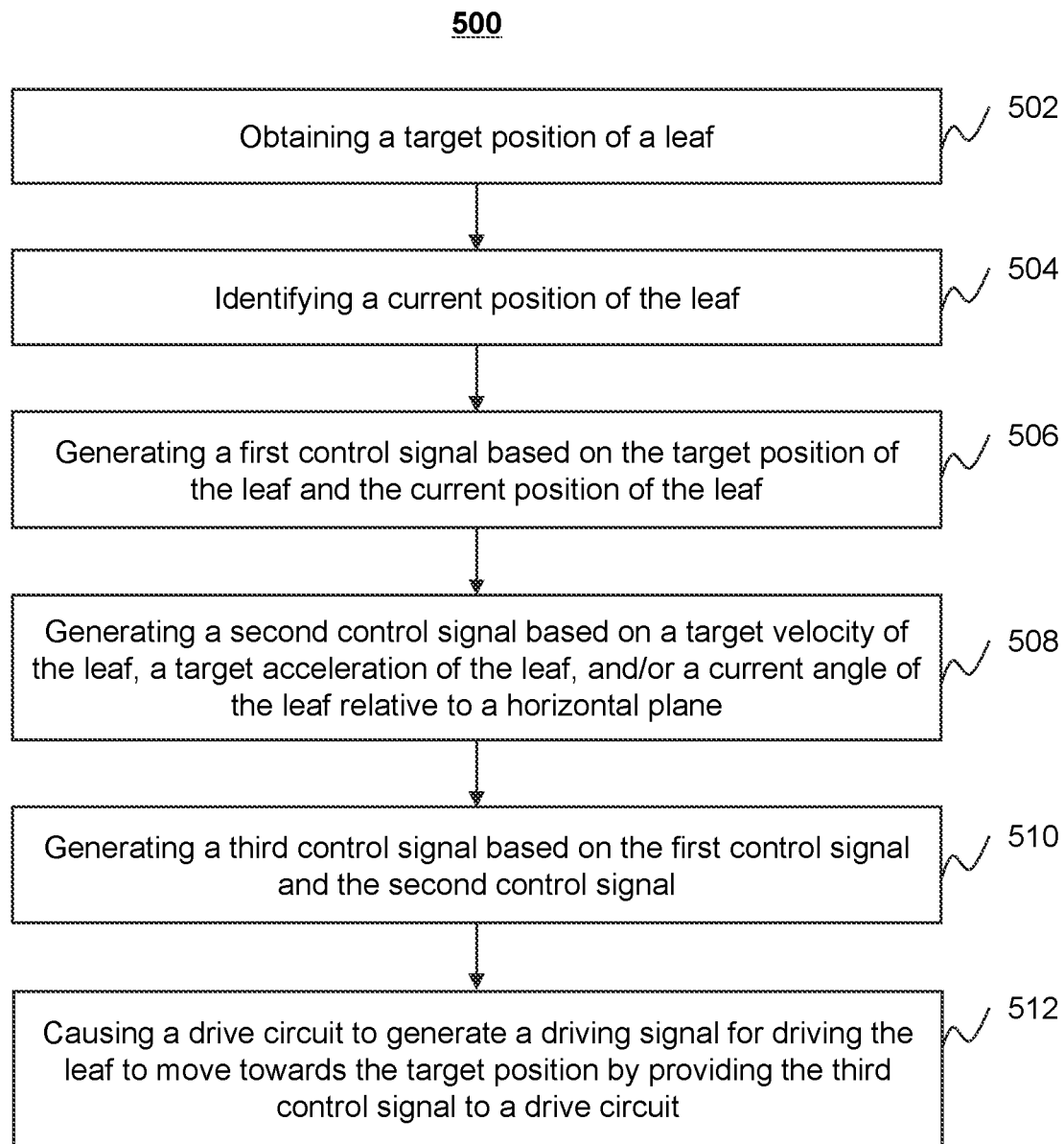
FIG. 5 is a flowchart illustrating an exemplary process for driving a leaf of a multi-leaf collimator according to some embodiments of the present disclosure.

FIG. 5 is a flowchart illustrating an exemplary process for driving a leaf of a multi-leaf collimator (MLC) according to some embodiments of the present disclosure. In some embodiments, at least part of process 500 may be performed by the processing device 140 (implemented in, for example, the computing device 200 shown in FIG. 2). For example, the process 500 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more units in the processing device 140 illustrated in FIG. 4). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In some embodiments, the process 500 may be performed after a radiation treatment planning process and/or a trajectory generation process. In some embodiments, in the treatment planning process, parameters such as a gantry speed, a leaf speed, a dose rate, or the like, and limits of one or more of the parameters may be considered. A plurality of discrete control points may be determined after the treatment planning process. A control point may identify a target position of a leaf. The trajectory generation process may generate a trajectory of leaf movement between two control points, and specify a variation of velocity with time (i.e., a velocity profile) (and/or a variation of acceleration with time (i.e., an acceleration profile)) of the leaf between the two control points. In some embodiments, the trajectory generation may be performed based on a trapezoidal velocity model, a double-s velocity model, etc. More descriptions of the trajectory generation process may be found in U.S. patent application Ser. No. 15/182,080 entitled "UNIFIED TRAJECTORY GENERATION PROCESS AND SYSTEM," filed Jun. 14, 2016, the contents of which are hereby incorporated by reference. The treatment planning process and the trajectory generation process can be performed according to any method known to persons having ordinary skills in the art. Therefore, one or more target positions (i.e., a position profile), one or more preset velocities, one or more preset accelerations of the leaves may be determined after the radiation treatment planning process and the trajectory generation process. In some embodiments, the target positions (i.e., the position profile), the preset velocities (i.e., the velocity profile), and/or the preset accelerations (i.e., the acceleration profile) may be stored in the storage device 150 for further use. In some embodiments, the process 500 may be performed in real time during a radiation treatment process based on the target positions, the preset velocities, and/or the preset accelerations of the leaves. It should be noted that although the process 500 illustrates the driving process of only one leaf, the other leaves in the MLC can be driven similarly.

In 502, a target position of a leaf may be obtained. The target position of the leaf may be obtained by the processing device 140 (e.g., the obtaining module 402) or the terminal(s) 130 (e.g., CPU 340). In some embodiments, the target position of the leaf may include a desired position of the leaf at a control point. In some embodiments, the target position of the leaf may include a desired position of the leaf between two control points. In some embodiments, a plurality of target positions of the leaf may be predetermined in the radiation treatment planning process and/or the trajectory generation process. For example, in some embodiments, a position profile illustrating a variation of position (between control points or target positions) with time may be obtained after trajectory generation, and the target position of the leaf corresponding to a next time point may be determined according to the position profile. In some embodiments, the target position of the leaf may be obtained from the storage device 150 or an external data source. It should be noted that although the process 500 illustrates only one target position, the movement of the leaf to the other target positions can be determined similarly; the movement of each of a plurality of leaves of the MLC to different target positions may be determined similarly.

In 504, a current position of the leaf may be identified. The current position of the leaf may be identified by the processing device 140 (e.g., the identification module 404). In some embodiments, the current position of the leaf may refer to an actual position of the leaf at the current time point during the treatment process. In some embodiments, the current position of the leaf may be detected by a position detection device (e.g., a displacement sensor, a Hall effect sensor, an encoder, a potentiometer, etc.). In some embodiments, the position detection device may detect signal(s) associated with the current position and/or the current velocity of the leaf. In some embodiments, the position detection device or other component(s) of the radiation delivery device 110 may further process the signal(s), and/or identify the current position and/or the current velocity of the leaf. In some embodiments, the radiation delivery device 110 may transmit the current position of the leaf to the processing device 140. In some embodiments, the radiation delivery device 110 may transmit the signal(s) associated with the current position and/or the current velocity of the leaf to the processing device 140, and the processing device 140 may further process the signal(s), and/or identify the current position of the leaf. More descriptions of the position detection device may be found elsewhere in the present disclosure (e.g., FIG. 1 and descriptions thereof).

In 506, a first control signal may be generated based on the target position of the leaf and the current position of the leaf. In some embodiments, the first control signal may be generated by the processing device 140 (e.g., the control signal generation module 406). In some embodiments, the first control signal may be configured to control a leaf speed (i.e., a motion speed of the leaf). In some embodiments, the first control signal may be in the form of a pulse width modulation (PWM) signal (see the first PWM signal 812 illustrated in FIG. 8). A PWM signal may be a way of generating an analog signal using a digital source (e.g., a digital signal). A PWM signal may include two main components that define its behavior: a duty cycle and a frequency. The duty cycle may describe the amount of time the control signal is in a high (i.e., on) state as a percentage of the total time it takes to complete one cycle. The frequency may determine how fast the PWM completes a cycle (e.g., 1000 Hz may correspond to 1000 cycles per second), and therefore how fast it switches between high and low states. In some embodiments, the processing device 140 may adjust the duty cycle of the PWM signal to achieve different leaf speeds.

In some embodiments, the first control signal may be generated through a closed-loop feedback control, and accordingly, the first control signal may be a feedback control signal. In some embodiments, the feedback control signal may be generated based on a difference between the target position of the leaf and the current position of the leaf. In some embodiments, the feedback control signal may be generated by inputting the difference between the target position of the leaf and the current position of the leaf to one or more control loops. Exemplary control loop(s) may include a position loop (see 808 in FIG. 8), a velocity loop (see 810 in FIG. 8), or the like, or any combination thereof. More descriptions of the generation of the first control signal may be found elsewhere in the present disclosure (e.g., FIGS. 6 and 8, and descriptions thereof).

In 508, a second control signal may be generated based on a target velocity of the leaf, a target acceleration of the leaf, and/or a current angle of the leaf. In some embodiments, the second control signal may be generated by the processing device 140 (e.g., the control signal generation module 406). In some embodiments, the second control signal may be configured to compensate the first control signal to control the leaf speed more efficiently and precisely. In some embodiments, the second control signal may also be in the form of a pulse width modulation (PWM) signal (see the second PWM signal 814 illustrated in FIG. 8).

In some embodiments, the second control signal may be generated through a feedforward control, and accordingly, the second control signal may be a feedforward control signal. In some embodiments, the feedforward control signal may be generated based on a first component associated with the target acceleration of the leaf, a second component associated with the target velocity of the leaf and/or the current angle of the leaf, and/or a third component associated with the current angle of the leaf. In some embodiments, the first component may be an acceleration feedforward control signal configured to reduce or eliminate the effect of the acceleration and/or deceleration on the leaf movement. The second component may be a friction feedforward control signal configured to reduce or eliminate the effect of the friction(s) (e.g., a slide friction and/or a viscous friction (see FIGS. 7 and 9-11)) on the leaf movement. The third component may be a gravity feedforward control signal configured to reduce or eliminate the effect of the change of gravity conditions during gantry (or MLC) rotation on the leaf movement. More descriptions of the second control signal may be found elsewhere in the present disclosure (e.g., FIGS. 7-11 and descriptions thereof).

In some embodiments, the target velocity of the leaf may include a desired velocity of the leaf corresponding to the next time point (or the next control point) immediately following the current time point (or the current control point) in a trajectory. In some embodiments, the target velocity of the leaf may be determined based on the velocity profile obtained in the trajectory generation process. In some embodiments, the target acceleration of the leaf may include a desired acceleration of the leaf corresponding to the next time point of the current time point in the trajectory between the two control points. In some embodiments, the target acceleration of the leaf may be determined based on the acceleration profile obtained in the trajectory generation process.

In some embodiments, the current angle of the leaf at a current time point may refer to an actual angle of the leaf at the current time point (e.g., relative to a horizontal plane) during the treatment process. In some embodiments, the MLC may be mounted on a collimator, and the collimator may be mounted on a gantry of the radiation delivery device 110, then the current angle of the MLC may be determined based on a current angle of the collimator relative to a predefined reference angle (e.g., 0°) of the collimator and a current angle of the gantry relative to a predefined reference angle (e.g., 0°) of the gantry. In some embodiments, the predefined reference angle (e.g., 0°) of the gantry may correspond to a position of the gantry when a component (e.g., the collimator) of the gantry is closest to the highest point of the gantry along the rotation trajectory of the gantry. In some embodiments, the predefined reference angle (e.g., 0°) of the collimator may correspond to a position of the collimator when the collimator is closest to the forefront of the gantry. In some embodiments, the current angle of the leaf at a current time point may be determined according to the following equation:

$$\sin(\alpha)=\sin(\beta)*\cos(\theta), \quad (1)$$

where $\alpha$ refers to the current angle of the leaf at the current time point, $\beta$ refers to the current angle of the gantry at the current time point relative to the predefined reference angle (e.g., 0°) of the gantry, $\theta$ refers to the current angle of the collimator at the current time point relative to the predefined reference angle (e.g., 0°) of the collimator. In some embodiments, the current angle of the leaf, the current angle of the gantry, and/or the current angle of the collimator at a current time point may be described in a coordinate system specified by International Electro Technical Commission (IEC). In some embodiments, the current angle of the gantry and/or the current angle of the collimator at a current time point may be obtained from a control system associated with the gantry and/or the collimator. In some embodiments, the current angle of the gantry and/or the current angle of the collimator at a current time point may be determined by an angle detection device (e.g., one or more angle sensors associated with the gantry and/or the collimator).

According to Equation (1), if the current angle of the collimator at a current time point is 0°, and the current angle of the gantry at the current time point is 90°, then the current angle of the leaf at the current time point may be determined as 90°. If the current angle of the collimator at a current time point is 90°, and the current angle of the gantry at the current time point is 0°, then the current angle of the leaf at the current time point may be determined as 0°. If the current angle of the collimator at a current time point is 45°, and the current angle of the gantry at the current time point is 45°, then the current angle of the leaf at the current time point may be determined as 30°. More descriptions of the determination of the current angle of the leaf may be found in Chinese Patent Application No. 201810960823.7 entitled "SYSTEMS AND METHODS FOR COMPENSATING A POSITION ERROR OF A MULTI-LEAF COLLIMATOR," filed Aug. 22, 2018, the contents of which are hereby incorporated by reference.

In 510, a third control signal may be generated based on the first control signal and the second control signal. The third control signal may be generated by the processing device 140 (e.g., the control signal generation module 406). In some embodiments, the third control signal may be generated based on the first control signal compensated by the second control signal. The third control signal may control the leaf speed more precisely and efficiently. In some embodiments, the third control signal may be in the form of a pulse width modulation (PWM) signal (see the compensated PWM signal 816 illustrated in FIG. 8). More descriptions of the third control signal may be found elsewhere in the present disclosure (e.g., FIG. 8 and descriptions thereof).

In 512, a drive circuit may be caused to generate a driving signal by providing the third control signal to the drive circuit. The leaf may be caused, according to the driving signal, to move towards the target position. In some embodiments, the processing device 140 (e.g., the driving signal generation module 408) may feed the third signal to the drive circuit so that the drive circuit may generate the driving signal accordingly. In some embodiments, the drive circuit may be mounted on and/or communicate with a radiation delivery device (e.g., the radiation delivery device 110). In some embodiments, the drive circuit may include one or more drive chips. In some embodiments, the driving signal may include an electric current generated by the drive chip(s). In some embodiments, the movement of the leaf towards the target position may be controlled by the processing device 140 (e.g., the control module 412) through the drive circuit.

Merely by way of example, in some embodiments, the third control signal may be provided or sent (e.g., by the processing device 140 (e.g., the transmission module 410)) to the drive circuit. In some embodiments, in response to the third control signal, the drive circuit may generate the driving signal to control the leaf to move towards the target position. Therefore, the leaf may be controlled to move (substantially) at the target acceleration of the leaf and the target velocity of the leaf, and approach the target position of the leaf. If motors are used as actuators, a direction and rotation speed of the motor(s) may be adjusted according to the driving signal to move the leaf towards the target position.

It should be noted that the above description of the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 502 and 504 may be integrated into a single operation. In some embodiments, the control signal generation module 406 may obtain the target position of the leaf, and identify the current position of the leaf.

Figure 6:
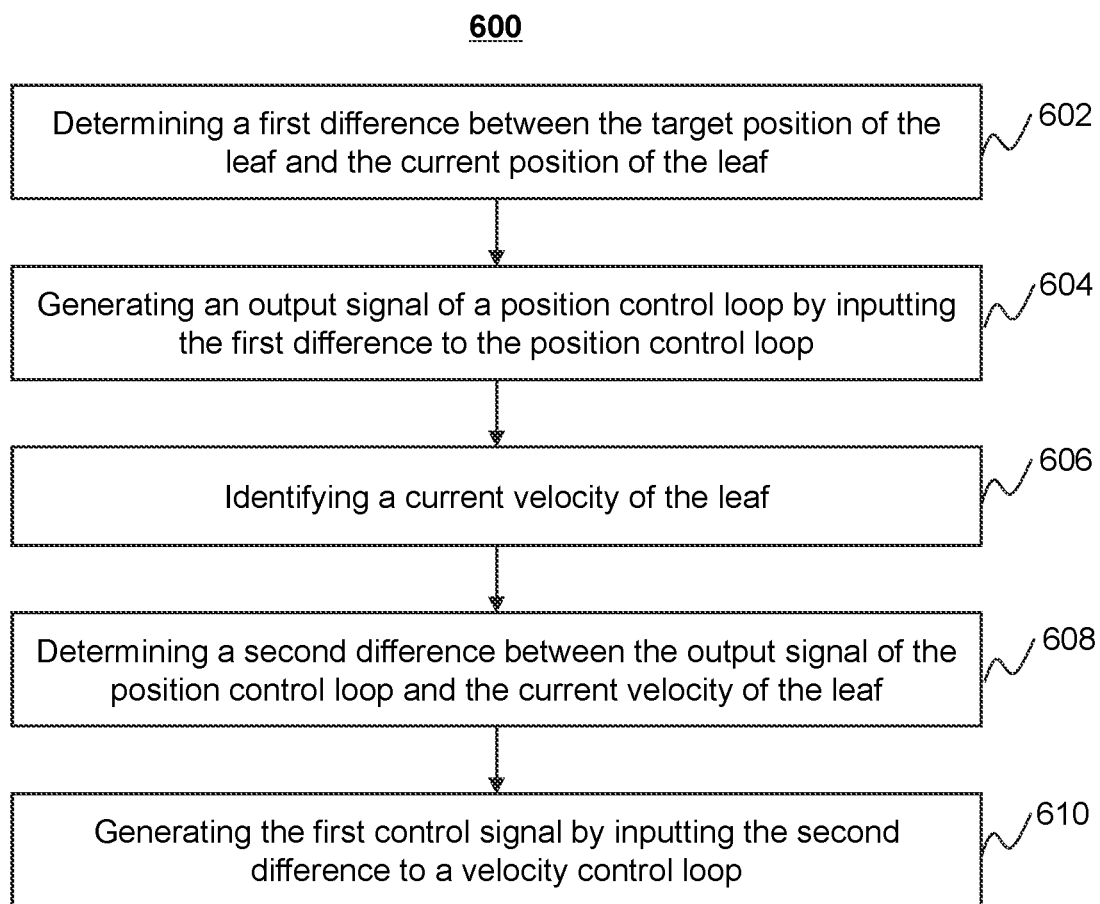
FIG. 6 is a flowchart illustrating an exemplary process for generating a feedback control signal according to some embodiments of the present disclosure.

FIG. 6 is a flowchart illustrating an exemplary process for generating a feedback control signal according to some embodiments of the present disclosure. In some embodiments, at least part of process 600 may be performed by the processing device 140 (implemented in, for example, the computing device 200 shown in FIG. 2). For example, the process 600 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more units in the processing device 140 illustrated in FIG. 4). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting. In some embodiments, operation 506 illustrated in FIG. 5 may be performed according to the process 600.

In 602, a first difference between the target position of the leaf (e.g., the target position of the leaf obtained in 502) and the current position of the leaf (e.g., the current position of the leaf identified in 504) may be determined. In some embodiments, the first difference between the target position of the leaf and the current position of the leaf may be determined by the processing device 140 (e.g., the control signal generation module 406). More descriptions of the target position and the current position may be found elsewhere in the present disclosure (e.g., the operations 502 and 504 in FIG. 5, and descriptions thereof). In some embodiments, the first difference (see the first difference signal 818 in FIG. 8) may be determined based on a difference between the current position (see the position feedback signal illustrated in FIG. 8) of the leaf and the target position (see the position profile signal illustrated in FIG. 8) of the leaf.

In 604, an output signal of a position control loop (e.g., the position loop 808 illustrated in FIG. 8) may be generated by inputting the first difference to the position control loop. In some embodiments, the output signal of the position control loop may be generated by the processing device 140 (e.g., the control signal generation module 406).

In some embodiments, the position control loop may receive the target position of the leaf and the current position of the leaf as input (or directly receive the first difference as input), and generate a velocity command as output. Specifically, in some embodiments, the first difference may be processed (e.g., gained or amplified) by a position proportional gain to generate the velocity command signal.

In some embodiments, the position control loop may receive the target position of the leaf, the current position of the leaf, and/or a gained target velocity of the leaf as input, and generate a velocity command signal as output. Specifically, the first difference may be processed (e.g., amplified or gained) by a position proportional gain, and the velocity command may be generated by summing the first gained difference and the gained target velocity. That is, in some embodiments, a feedforward velocity control may be introduced in the generation of the velocity command signal using the position control loop. More descriptions of the position control loop may be found elsewhere in the present disclosure (e.g., FIG. 8 and descriptions thereof).

In 606, a current velocity of the leaf (see the velocity feedback signal illustrated in FIG. 8) may be identified. The current velocity of the leaf may be identified by the processing device 140 (e.g., the identification module 404). In some embodiments, the current velocity of the leaf at a current time point may refer to an actual velocity of the leaf at the current time point during the treatment process. In some embodiments, the current velocity of the leaf may be detected by a position detection device (e.g., a Hall effect sensor, an encoder, a potentiometer, etc.). In some embodiments, the position detection device may detect signal(s) associated with the current position and/or the current velocity of the leaf. In some embodiments, the position detection device or other component(s) of the radiation delivery device 110 may further process the signal(s), and/or identify the current positon and/or the current velocity of the leaf. In some embodiments, the radiation delivery device 110 may transmit the current velocity of the leaf to the processing device 140. In some embodiments, the radiation delivery device 110 may transmit the signal(s) associated with the current position and/or the current velocity of the leaf to the processing device 140, and the processing device 140 may further process the signal(s), and/or identify the current velocity of the leaf. More descriptions of the position detection device may be found elsewhere in the present disclosure (e.g., FIG. 1 and descriptions thereof).

In 608, a second difference between the output signal of the position control loop and the current velocity of the leaf may be determined. In some embodiments, the second difference between the output signal of the position control loop and the current velocity of the leaf may be determined by the processing device 140 (e.g., the control signal generation module 406). In some embodiments, the second difference (see the second difference signal 820 in FIG. 8) may be determined based on a difference between the current velocity (see the velocity feedback signal illustrated in FIG. 8) of the leaf and the output signal of the position control loop (see the velocity command signal illustrated in FIG. 8).

Figure 8:
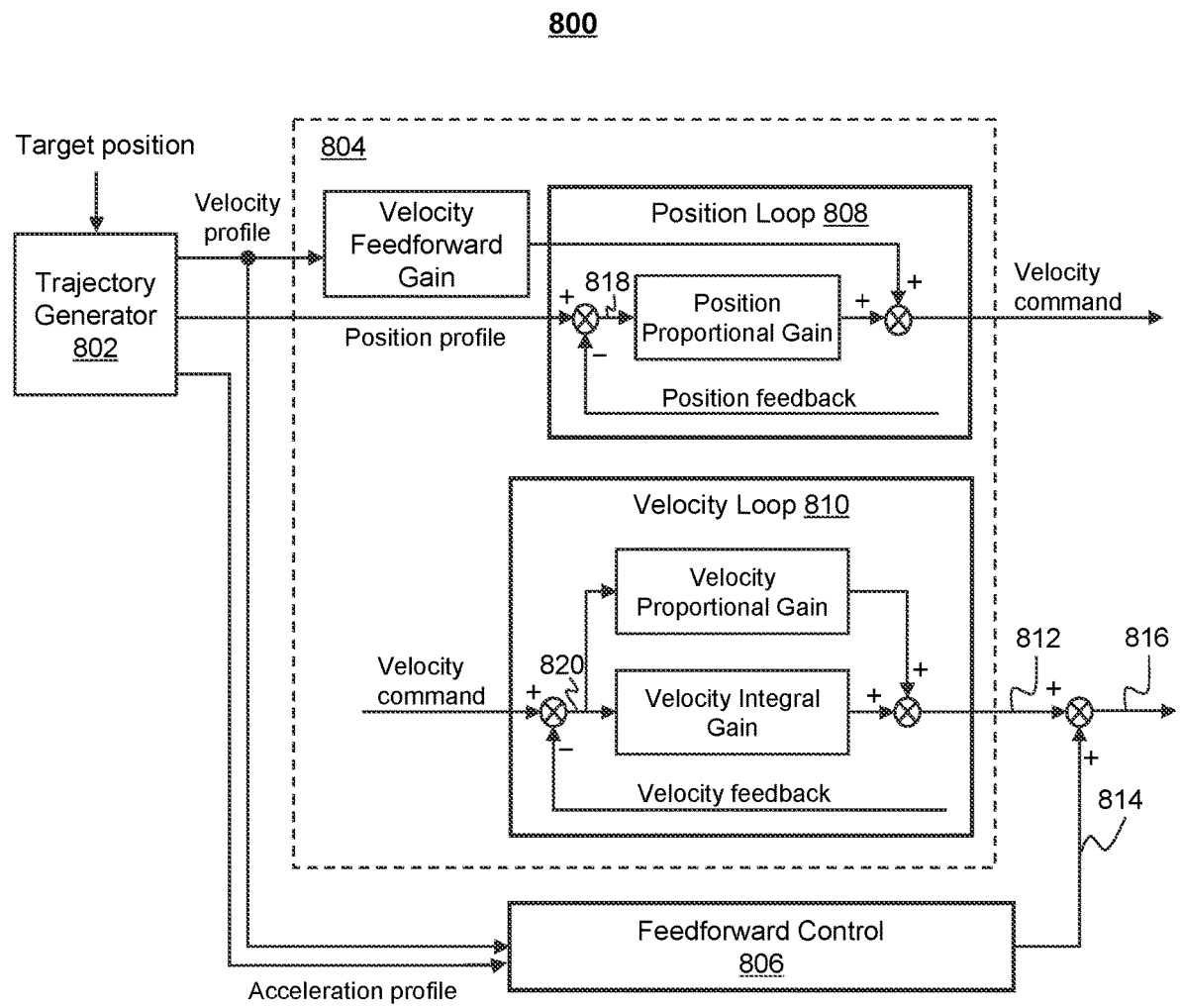
FIG. 8 is a block diagram illustrating an exemplary control system for generating a compensated control signal using a feedback control and a feedforward control according to some embodiments of the present disclosure.

In 610, the first control signal may be generated by inputting the second difference to a velocity control loop (e.g., the velocity loop 810 in FIG. 8). In some embodiments, the first control signal may be generated by the processing device 140 (e.g., the control signal generation module 406). In some embodiments, the velocity control loop may receive the output signal of the position control loop and the current velocity as input (or directly receive the second difference as input), and generate the first control signal (see the first PWM signal 812 illustrated in FIG. 8). More descriptions of the velocity control loop may be found elsewhere in the present disclosure (e.g., FIG. 8 and descriptions thereof).

It should be noted that the above description of the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 606 and 608 may be integrated into a single operation.

Figure 7:
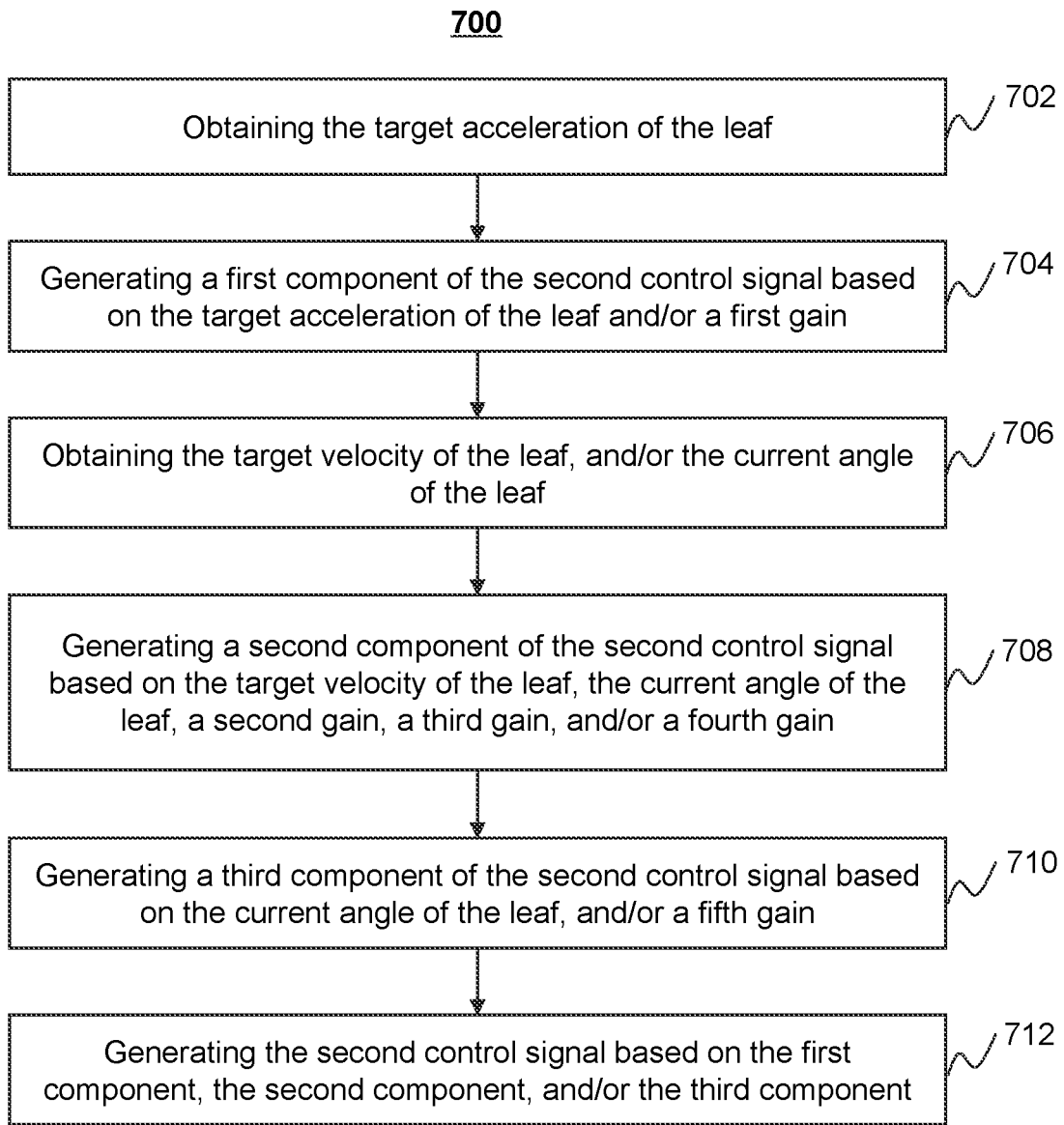
FIG. 7 is a flowchart illustrating an exemplary process for generating a feedforward control signal according to some embodiments of the present disclosure.

FIG. 7 is a flowchart illustrating an exemplary process for generating a feedforward control signal according to some embodiments of the present disclosure. In some embodiments, at least part of process 700 may be performed by the processing device 140 (implemented in, for example, the computing device 200 shown in FIG. 2). For example, the process 700 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more units in the processing device 140 illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting. In some embodiments, operation 508 illustrated in FIG. 5 may be performed according to the process 700.

In 702, the target acceleration of the leaf may be obtained. In some embodiments, the target acceleration of the leaf may be obtained by the processing device 140 (e.g., the obtaining module 402). In some embodiments, the target acceleration of the leaf may be obtained from the storage device 150 or an external data source. More descriptions of the target acceleration of the leaf may be found elsewhere in the present disclosure (e.g., FIG. 5 and descriptions thereof).

In 704, a first component of the second control signal may be generated based on the target acceleration of the leaf, and/or a first gain. In some embodiments, the first component of the second control signal may be generated by the processing device 140 (e.g., the control signal generation module 406).

In some embodiments, the first component of the second control signal may be an acceleration feedforward control signal. In some embodiments, the acceleration feedforward control signal may be configured to compensate an acceleration error between the target acceleration and the current acceleration of the leaf (i.e., a difference between the target acceleration and the current acceleration of the leaf), and eliminate (or reduce) the acceleration lag(s). In some embodiments, the acceleration feedforward control signal may relate to the target acceleration of the leaf and a first gain corresponding to the acceleration feedforward control (i.e., an acceleration feedforward gain). In some embodiments, the acceleration feedforward control signal may be generated according to Equation (2) as illustrated below:

$$\text{AccelerationFF} = K_a * \text{ref\_a},\qquad(2)$$

where AccelerationFF refers to the acceleration feedforward control signal (i.e., the first component of the second control signal), Ka refers to the first gain corresponding to the acceleration feedforward control, ref_a refers to the target acceleration of the leaf. In some embodiments, Ka may relate to the mass of the leaf, and/or one or more characteristics of the drive circuit. The characteristics of the drive circuit may include a driving power (e.g., a driving voltage), a driving circuit (e.g., an impedance of the driving circuit, one or more parameters of electronic component(s) of the drive circuit, or the like), and/or one or more characteristics of driving motors. In some embodiments, Ka may be predetermined according to one or more experimental tests.

In an exemplary experimental test, the gantry may be positioned at an initial angle of 0°. In some embodiments, if the angle of the collimator (e.g., the angle of the housing of the MLC) is 90°, or the angle of the gantry is 0°, the initial angle of the leaf (e.g., relative to the horizontal plane) may be 0°. A plurality of velocity curves may be detected by driving the leaf to move from a stationary state and/or at the initial angle of the leaf under a plurality of fourth control signals. In some embodiments, a fourth control signal may refer to a PWM signal used for driving the leaf to move from a stationary state. In some embodiments, the fourth control signals may be generated by a control device of the MLC (e.g., the processing device 140). An operator may set desired PWM duty cycle(s) through the control device. For example, the operator may set the PWM duty cycle as 20% at first to drive the leaf to move from a stationary state. Then the PWM duty cycle may be increased by 20% for several times (i.e., 40%, 60%, 80%, 100%) and be used to drive the leaf to move from a stationary state again. Each time the PWM duty cycle is increased by 20%, the leaf may be driven to move from a stationary state again. Under each of the plurality of fourth control signals, a velocity curve may be obtained, and an acceleration may be determined by calculating the derivative of the velocity curve. Thus, a plurality of accelerations may be obtained based on the plurality of velocity curves, and accordingly, an acceleration curve illustrating a relation between the plurality of accelerations and the plurality of the fourth control signals may be generated. In some embodiments, a slope of the acceleration curve may be designated as the first gain (i.e., Ka). In some embodiments, the slope of the acceleration curve may be determined based on a least-square algorithm. In some embodiments, in the determination of the first gain, the closed-loop feedback control signal (e.g., the feedback control signal) may not be used (or the feedback control signal be set as 0).

In 706, the target velocity of the leaf, and/or the current angle of the leaf may be obtained. In some embodiments, the target velocity of the leaf, and/or the current angle of the leaf may be obtained by the processing device 140 (e.g., the obtaining module 402). In some embodiments, the target velocity of the leaf may be obtained from the storage device 150 or an external data source. In some embodiments, the current angle of the leaf may be obtained based on the current angle of the collimator and the current angle of the gantry. More descriptions of the target velocity of the leaf, and/or the current angle of the leaf may be found elsewhere in the present disclosure (e.g., operation 508 in FIG. 5 and descriptions thereof).

In 708, a second component of the second control signal may be generated based on the target velocity of the leaf, the current angle of the leaf, a second gain, a third gain, and/or a fourth gain. In some embodiments, the second component of the second control signal may be generated by the processing device 140 (e.g., the control signal generation module 406).

In some embodiments, the second component of the second control signal may be a friction feedforward control signal. In some embodiments, the friction feedforward control signal may be used to compensate the position error and/or the velocity error to eliminate (or reduce) the position lag(s) and/or the velocity lag(s). In some embodiments, the frictions in the leaf movement may include one or more slide frictions (see FIGS. 9-10), one or more viscous frictions, etc. Accordingly, the friction feedforward control signal may include a slide friction feedforward control signal, and/or a viscous friction feedforward control signal. In some embodiments, the second component of the second control signal may be determined by summing the slide friction feedforward control signal (see, e.g., Equation (3)) and the viscous friction feedforward control signal (see, e.g., Equation (5)).

Merely by way of example with reference to Equations (3) and (5), a first product of a cosine of the current angle of the leaf multiplied by the second gain may be determined; a second product of a sine of the current angle of the leaf multiplied by the third gain may be determined; a sum of the first product and the second product may be determined; the sum may be adjusted according to a direction of the target velocity of the leaf; and/or a third product of the target velocity of the leaf multiplied by the fourth gain may be determined; and the second component of the second control signal may be generated based on the sum and the third product.

In some embodiments, the slide friction feedforward control signal may relate to a direction of the target velocity of the leaf, the current angle of the leaf, a second gain corresponding to the slide friction feedforward control in the horizontal direction (i.e., a slide friction feedforward gain in the horizontal direction), and/or a third gain corresponding to the slide friction feedforward control in the gravity direction (i.e., a slide friction feedforward gain in the gravity direction).

Figure 11:
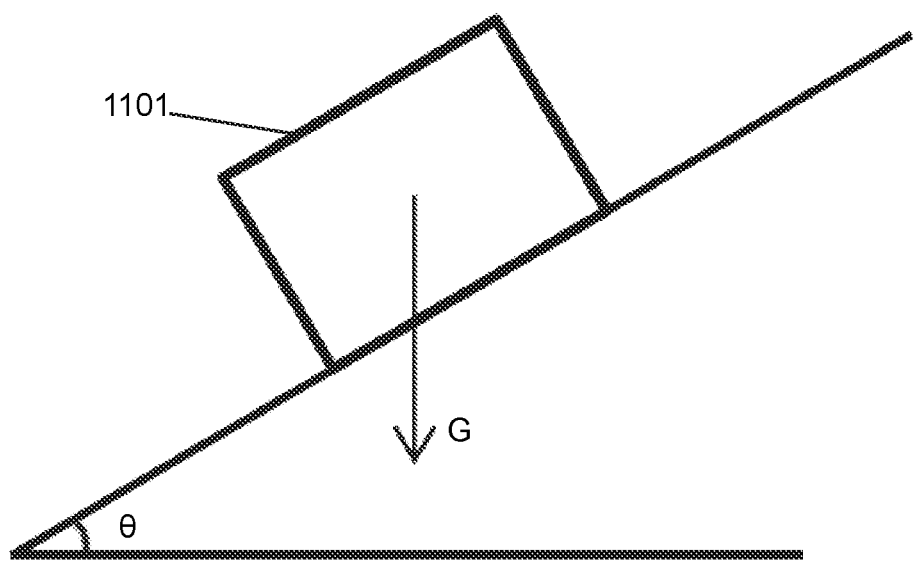
FIG. 11 is a schematic diagram illustrating an exemplary pressure of a leaf at an angle θ according to some embodiments of the present disclosure.

In some embodiments, the slide friction feedforward control signal may be generated according to Equation (3) as illustrated below:

$$\text{SlideFrictionFF}=K_{sf\_h}*\text{sign}(\text{ref}\_v)*\cos\theta+K_{sf\_v}*\text{sign}(\text{ref}\_v)*\sin\theta, \qquad (3)$$

where SlideFrictionFF refers to the slide friction feedforward control signal, $K_{sf\_h}$ refers to the second gain (i.e., the slide friction feedforward gain in the horizontal direction), $K_{sf\_v}$ refers to the third gain (i.e., the slide friction feedforward gain in the gravity direction), sign(ref_v) refers to the direction of the target velocity of the leaf, ref_v refers to the target velocity of the leaf, θ refers to the current angle of the leaf, cos θ refers to a pressure coefficient of the leaf in the horizontal direction (see FIG. 11), and sin θ, refers to a pressure coefficient of the leaf in the gravity direction (see FIG. 11). In some embodiments, the second gain $K_{sf\_h}$ and/or the third gain $K_{sf\_v}$ may be predetermined according to one or more experimental tests.

In an exemplary experimental test, the gantry may be positioned at an initial angle of 0°. In some embodiments, if the angle of the collimator is 90°, or the angle of the gantry is 0°, the initial angle of the leaf (e.g., relative to the horizontal plane) may be 0°. The leaf may be driven to move from a stationary state and/or at the initial angle of the leaf by increasing (e.g., from 0 to a critical value) a fourth control signal, and accordingly, the leaf may start to move under the fourth control signal with the critical value. The critical value may refer to a threshold. If the fourth control signal exceeds the threshold, the leaf may start to move. In some embodiments, the fourth control signal may be generated by a control device of the MLC (e.g., the processing device 140). An operator may set desired PWM duty cycle(s) through the control device. In some embodiments, the second gain $K_{sf\_h}$ may be determined based on the critical value. In some embodiments, the critical value may be directly designated as the second gain $K_{sf\_h}$. For example, if the critical value is 60%, $K_{sf\_h}$ may be determined as 60%. In some embodiments, the critical value multiplied by a coefficient (e.g., a coefficient less than 1 (e.g., 0.9)) may be a designated as the second gain $K_{sf\_h}$. For example, if the critical value is 60%, $K_{sf\_h}$ may be determined as 54%. In some embodiments, in the determination of the second gain, the closed-loop feedback control signal (e.g., the feedback control signal) may not be used (or the feedback control signal be set as 0).

In an exemplary experimental test, the gantry may be positioned at an angle of 90°, and the collimator may be positioned at an initial ganle of 0°. In some embodiments, if the angle of the collimator is 0°, and the angle of the gantry is 90°, the initial angle of the leaf (e.g., relative to the horizontal plane) may be 90°. In some embodiments, the leaf may be driven to move upwards from a stationary state and/or at the initial angle of the leaf by increasing (e.g., from 0 to a first critical value) a fourth control signal, and accordingly, the leaf may start to move upwards under the fourth control signal with the first critical value. In some embodiments, the leaf may be driven to move downwards from a stationary state and/or at the initial angle of the leaf by increasing (e.g., from 0 to a second critical value) a fourth control signal, and accordingly, the leaf may start to move downwards under the fourth control signal with the second critical value. The first critical value may refer to a first threshold. If the fourth control signal exceeds the first threshold, the leaf may start to move upwards. The second critical value may refer to a second threshold. If the fourth control signal exceeds the second threshold, the leaf may start to move downwards. In some embodiments, the third gain $K_{sf\_v}$ may be determined based on a difference between the first critical value and the second critical value, as illustrated in Equation (4):

$$K_{sf\_v}=(\text{PWM}_1-\text{PWM}_2)/2, \qquad (4)$$

where $\text{PWM}_1$ refers to the first critical value, $\text{PWM}_2$ refers to the second critical value. For example, if the first critical value is 80%, the second critical value is 30%, then $K_{sf}$ may be determined as 25%. In some embodiments, in the determination of the third gain, the closed-loop feedback control signal (e.g., the feedback control signal) may not be used (or the feedback control signal be set as 0).

In some embodiments, the viscous friction feedforward control signal may relate to the target velocity of the leaf, and/or a fourth gain corresponding to the viscous friction feedforward control (i.e., a viscous friction feedforward gain). In some embodiments, the viscous friction feedforward control signal may be generated according to Equation (5) as illustrated below:

$$\text{ViscousfrictionFF}=K_{vf}*\text{ref}\_v, \qquad (5)$$

where ViscousfrictionFF refers to the viscous friction feedforward control signal, $K_{vf}$ refers to the fourth gain (i.e., the viscous friction feedforward gain), ref_v refers to the target velocity of the leaf. In some embodiments, the fourth gain $K_{vf}$ may be predetermined according to one or more experimental tests.

In an exemplary experimental test, the gantry may be positioned at an inigial angle of 0°. In some embodiments, if the angle of the collimator is 90°, or the angle of the gantry is 0°, the initial angle of the leaf (e.g., relative to the horizontal plane) may be 0°. In some embodiments, a plurality of velocities of the leaf in a steady-state motion and/or at the initial angle of the leaf under a plurality of fourth control signals may be detected. In some embodiments, the fourth control signals may be generated by a control device of the MLC (e.g., the processing device 140). An operator may set desired PWM duty cycle(s) through the control device. In some embodiments, a velocity curve illustrating a relation between the plurality of velocities and the plurality of fourth control signals may be generated. In some embodiments, a slope of the velocity curve may be designated as the fourth gain $K_{vf}$. In some embodiments, the slope of the velocity curve may be determined based on a least-square algorithm. In some embodiments, in the determination of the fourth gain, the closed-loop feedback control signal (e.g., the feedback control signal) may not be used (or the feedback control signal be set as 0).

In 710, a third component of the second control signal may be generated based on the current angle of the leaf, and/or a fifth gain. In some embodiments, the third component of the second control signal may be generated by the processing device 140 (e.g., the control signal generation module 406). In some embodiments, the third component of the second control signal may be a gravity feedforward control signal. In some embodiments, the gravity feedforward control signal may be configured to reduce or eliminate the effect of the change of gravity conditions during gantry (or MLC) rotation on the leaf movement. In some embodiments, the third component of the second control signal may relate to the current angle of the leaf, and/or a fifth gain corresponding to the gravity feedforward control (i.e., a gravity feedforward gain). In some embodiments, the gravity feedforward control signal may be generated by multiplying a sine of the current angle of the leaf by the fifth gain, as illustrated below:

$$GravityFF = K_g * \sin \theta, \quad (6)$$

where GravityFF refers to the gravity feedforward control signal, $K_g$ refers to a fifth gain (i.e., the gravity feedforward gain), θ refers to the current angle of the leaf (see FIG. 11).

In some embodiments, $K_g$ may be predetermined according to one or more experimental tests similar to those described in operation 708. For example, $K_g$ may be determined according to Equation (7) as illustrated below:

$$K_g = (PWM_1 + PWM_2)/2, \quad (7)$$

where $PWM_1$ refers to the first critical value described in operation 708, $PWM_2$ refers to the second critical value described in operation 708. For example, if the first critical value is 80%, and the second critical value is 30%, then $K_g$ may be determined as 55%. In some embodiments, in the determination of the fifth gain, the closed-loop feedback control signal (e.g., the feedback control signal) may not be used (or the feedback control signal be set as 0).

In 712, the second control signal may be generated based on the first component, the second component, and/or the third component. In some embodiments, the second control signal may be generated by the processing device 140 (e.g., the control signal generation module 406). In some embodiments, the second control signal may be generated based on a sum of the first component, the second component, and/or the third component, as illustrated in Equation (8):

$$TotalFF = AccelerationFF + SlideFrictionFF + ViscousfrictionFF + GravityFF, \quad (8)$$

where TotalFF refers to the second control signal.

It should be noted that the above description of the process 700 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the process 700 may further include operations for obtaining the first gain, the second gain, the third gain, the fourth gain, and/or the fifth gain. In some embodiments, one or more of the operations regarding the generation of the components of the second control signal may be omitted. For example, operation 704 may be omitted, and the second control signal may be determined based on the second component and the third component. As another example, operation 708 may be omitted, and the second control signal may be determined based on the first component and the third component. As a further example, operation 710 may be omitted, and the second control signal may be determined based on the first component and the second component.

FIG. 8 is a block diagram illustrating an exemplary control system for generating a compensated control signal using a feedback control and a feedforward control according to some embodiments of the present disclosure. In some embodiments, a third control signal (i.e., the compensated control signal) may be generated by the processing device 140 (e.g., the control signal generation module 406). The control system 800 may include a feedback control 804, and a feedforward control 806. The feedback control 804 may generate a first PWM signal 812. The feedforward control 806 may generate a second PWM signal 814. A compensated PWM signal 816 may be generated based on the first PWM signal 812 and the second PWM signal 814 (e.g., by summing the first PWM signal 812 and the second PWM signal 814).

In some embodiments, the trajectory generator 802 may generate trajectories of a leaf of the MLC based on one or more control points (i.e., target position(s)) determined in a treatment planning process. Specifically, as shown in FIG. 8, the trajectory generator 802 may generate a velocity profile, a position profile, and/or an acceleration profile. A velocity profile may illustrate a variation of the target velocity of the leaf with time, and a target velocity of the leaf may correspond to a velocity in the velocity profile at a time point. A position profile may illustrate a variation of the target position of the leaf with time, and a target position of the leaf may correspond to a position in the velocity profile at a time point. An acceleration profile may illustrate a variation of the target acceleration of the leaf with time, and a target acceleration of the leaf may correspond to an acceleration in the velocity profile at a time point. In some embodiments, the trajectory generator 802 may be omitted from the control system 800, and accordingly, the velocity profile, position profile, and/or the acceleration profile may be obtained from the storage device 150.

In some embodiments, the feedback control 804 may generate the first PWM signal 812 using a proportional-integral-differential (PID) control technology. The feedback control 804 may include a position loop 808 and a velocity loop 810. In some embodiments, the position loop 808 may receive the position profile, a position feedback signal, and/or a gained velocity profile as input, and generate a velocity command signal. Specifically, a first difference signal 818 may be obtained based on the position profile and the position feedback signal (e.g., by subtracting the position feedback signal from the position profile). More descriptions of the position feedback signal may be found elsewhere in the present disclosure (e.g., FIGS. 1 and 5, and descriptions thereof). The first difference signal 818 may be processed (e.g., amplified or gained) by a position proportional gain. The velocity profile may be processed (e.g., amplified or gained) by a velocity feedforward gain to generate a gained velocity profile. The velocity command signal may be generated by summing the first gained difference signal and the gained velocity profile.

In some embodiments, the velocity loop 810 may receive the velocity command signal, and/or a velocity feedback signal as input, and generate a first PWM signal 812. Specifically, a second difference signal 820 may be obtained based on the velocity command signal and the velocity feedback signal (e.g., by subtracting the velocity feedback signal from the velocity command signal). More descriptions of the velocity feedback signal may be found elsewhere in the present disclosure (e.g., FIGS. 1 and 5, and descriptions thereof). The second difference signal 820 may be processed (e.g., amplified or gained) by a velocity proportional gain to obtain a second proportionally gained difference signal. The second difference signal 820 may also be processed (e.g., amplified or gained) by a velocity integral gain to obtain a second integrally gained difference signal. The first PWM signal 812 may be obtained by summing the second proportionally gained difference signal and the second integrally gained difference signal.

The feedforward control 806 may receive the velocity profile, the acceleration profile, and/or the current angle of the leaf (not shown in FIG. 8) as input, and generate a second PWM signal 814. Specifically, the feedforward control 806 may generate a first component of the second PWM signal 814 based on the acceleration profile, generate a second component of the second PWM signal 814 based on the velocity profile and/or the current angle of the leaf, and/or generate a third component of the second PWM signal 814 based on the current angle of the leaf. In some embodiments, the feedforward control 806 may generate the second PWM signal 814 based on the first component, the second component, and/or the third component (e.g., by summing the first component, the second component, and/or the third component). More descriptions of the generation of different components of the second PWM signal 814 may be found elsewhere in the present disclosure (e.g., FIG. 7 and descriptions thereof).

It should be noted that the above description of the control system 800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 9:
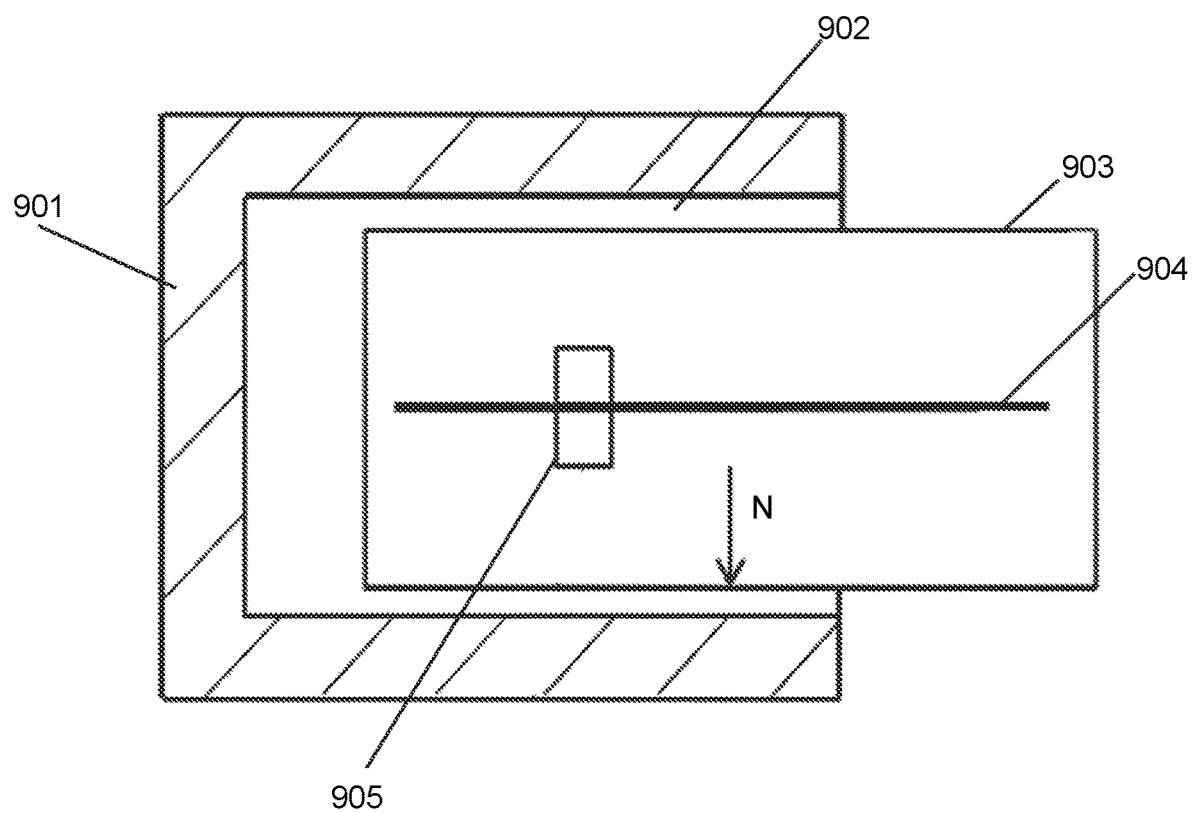
FIG. 9 is a schematic diagram illustrating an exemplary slide friction of a leaf of an MLC when the leaf moves in a horizontal direction according to some embodiments of the present disclosure.
Figure 10:
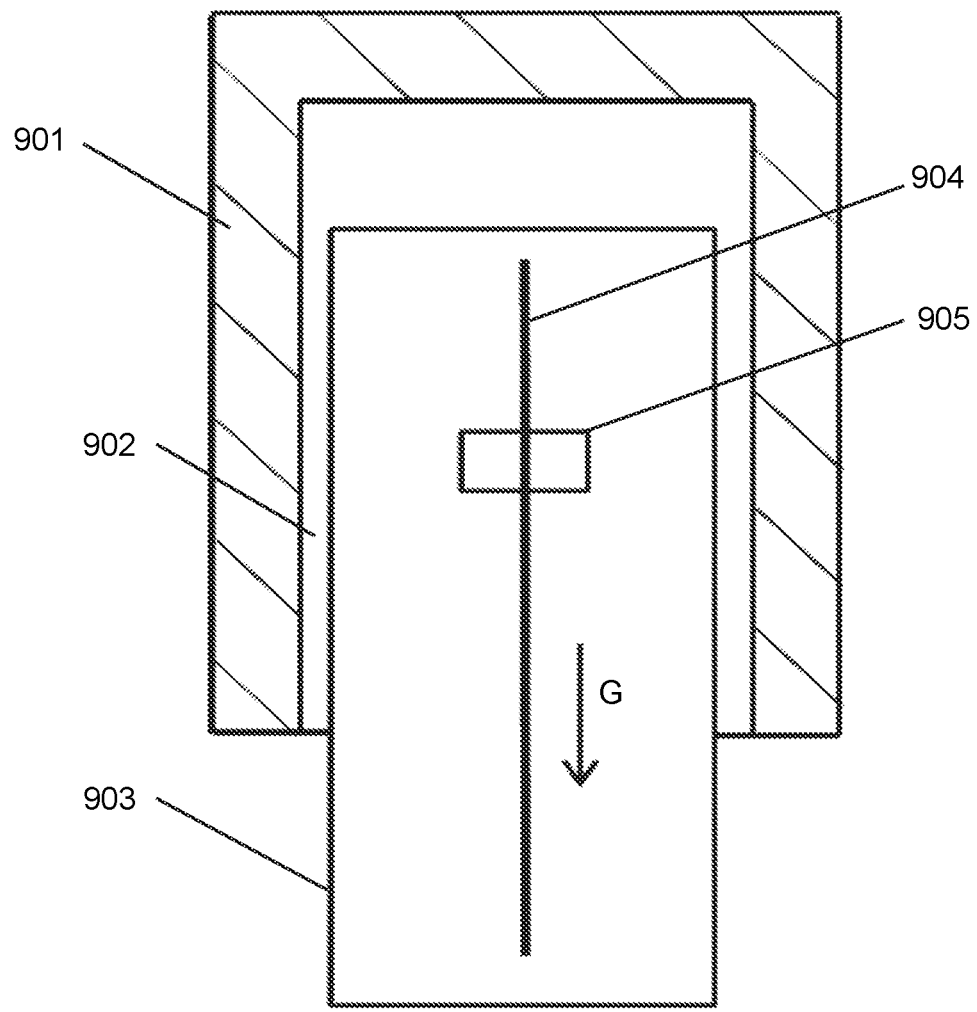
FIG. 10 is a schematic diagram illustrating an exemplary slide friction of a leaf of an MLC when the leaf moves in a gravity direction according to some embodiments of the present disclosure.

FIG. 9 is a schematic diagram illustrating an exemplary slide friction of a leaf of an MLC when the leaf moves in a horizontal direction according to some embodiments of the present disclosure. FIG. 10 is a schematic diagram illustrating an exemplary slide friction of a leaf of an MLC when the leaf moves in a gravity direction according to some embodiments of the present disclosure. FIGS. 9-10 show a section view of the MLC. As shown in FIGS. 9-10, the MLC may include a housing 901, a leaf guide 902, one or more leaves 903, one or more screws 904, and one or more screw nuts 905. A motion of the screw 904 relative to the screw nut 905 may be driven by an actuator (e.g., a motor). The motion of the screw 904 relative to the screw nut 905 may cause the leaf 903 to move. In some embodiments, the housing 901 may be driven to move and bring the leaf 903 to move. In some embodiments, the leaf 903 may be driven to move relative to the housing 901. In some embodiments, the housing 901 and the leaf 903 may move independently.

As shown in FIG. 9, when the leaf 903 moves in the horizontal direction, a slide friction between the leaf 903 and the leaf guide 902 may act on the leaf 903. When the housing 901 moves in the horizontal direction, a slide friction between the housing 901 and a guide rail (not shown in FIG. 9) that guides the housing 901 to move may act on the housing. In some embodiments, the slide friction of the leaf 903 may relate to a pressure N (between the leaf 903 and the leaf guide 902) perpendicular to the friction direction (i.e., the gravity of the leaf 903). In some embodiments, the slide friction of the housing 901 may relate to a pressure (between the housing 901 and the guide rail) perpendicular to the friction direction (i.e., the gravity of the housing 901).

As shown in FIG. 10, when the leaf 903 moves in the gravity direction, the gravity of the leaf 903 is G, the pressure between the leaf 903 and the leaf guide 902 may be 0, and accordingly, the slide friction between the leaf 903 and the leaf guide 902 may be 0. Similarly, when the housing 901 moves in the gravity direction, the pressure between the housing 901 and the guide rail may be 0, and accordingly, the slide friction between the housing 901 and the guide rail may be 0. However, a slide friction between the screw 904 and the screw nut 905 may exist.

FIG. 11 is a schematic diagram illustrating an exemplary pressure of a leaf at an angle θ according to some embodiments of the present disclosure. As shown in FIG. 11, the pressure of the leaf 1101 at the angle θ (0°≤θ≤90°) may be determined based on an inclined plane model. In some embodiments, the pressure of the leaf 1101 at the angle θ may relate to a first pressure coefficient of the leaf 1101 in the horizontal direction, and/or a second pressure coefficient of the leaf in the gravity direction. In some embodiments, the first pressure coefficient may be a cosine of the angle θ. In some embodiments, the second pressure coefficient may be a sine of the angle θ. And the slide friction(s) of the leaf 1101 may be determined in the horizontal direction and the gravity direction based on the first pressure coefficient and the second pressure coefficient, respectively, as illustrated in FIGS. 9-10.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for driving a leaf of a multi-leaf collimator (MLC) implemented on a machine including at least a processor and a storage device, comprising:
obtaining a target position of the leaf;
identifying a current position of the leaf;

generating a first control signal based on the target position of the leaf and the current position of the leaf;
generating a second control signal based on at least one of a target velocity of the leaf, a target acceleration of the leaf, or a current angle of the leaf, wherein the second control signal is generated by a following process, including:
  obtaining the target acceleration of the leaf, and
  generating a first component of the second control signal based on the target acceleration of the leaf and a first gain;
generating a third control signal based on the first control signal and the second control signal; and
causing a drive circuit to generate a driving signal for driving the leaf to move towards the target position by providing the third control signal to the drive circuit.

2. The method of claim 1, wherein the generating a first component of the second control signal based on the target acceleration of the leaf and a first gain comprises:
  generating the first component of the second control signal by multiplying the target acceleration of the leaf by the first gain.

3. The method of claim 1, wherein the first gain relates to a mass of the leaf and a characteristic of the drive circuit.

4. The method of claim 1, wherein the MLC is mounted on a gantry, and the first gain is determined according to a process including:
  positioning the gantry at an initial angle of 0°;
  detecting a plurality of velocity curves by driving the leaf to move from a stationary state under a plurality of fourth control signals;
  generating, based on the plurality of velocity curves, an acceleration curve illustrating a relation between a plurality of accelerations and the plurality of fourth control signals; and
  designating a slope of the acceleration curve as the first gain.

5. The method of claim 1, wherein the generating a second control signal based on at least one of a target velocity of the leaf, a target acceleration of the leaf, or a current angle of the leaf comprises:
  obtaining the target velocity of the leaf and the current angle of the leaf; and
  generating a second component of the second control signal based on the target velocity of the leaf, the current angle of the leaf, and at least one of a second gain, a third gain, or a fourth gain.

6. The method of claim 5, wherein the generating a second component of the second control signal comprises:
  determining a first product of a cosine of the current angle of the leaf multiplied by the second gain;
  determining a second product of a sine of the current angle of the leaf multiplied by the third gain;
  determining a sum of the first product and the second product;
  adjusting the sum according to a direction of the target velocity of the leaf;
  determining a third product of the target velocity of the leaf multiplied by the fourth gain; and
  generating the second component of the second control signal based on the sum and the third product.

7. The method of claim 5, wherein the MLC is mounted on a gantry, and the second gain is determined according to a process including:
  positioning the gantry at an initial angle of 0°;
  driving the leaf to move from a stationary state by increasing, from 0 to a critical value, a fourth control signal, in which the leaf starts to move under the fourth control signal with the critical value; and
  determining the second gain based on the critical value.

8. The method of claim 5, wherein the MLC is mounted on a collimator, the collimator is mounted on a gantry, and the third gain is determined according to a process including:
  positioning the gantry at an angle of 90°;
  positioning the collimator at an initial angle of 0°;
  driving the leaf to move upwards from a stationary state by increasing, from 0 to a first critical value, a fourth control signal, in which the leaf starts to move upwards under the fourth control signal with the first critical value;
  driving the leaf to move downwards from a stationary state by increasing, from 0 to a second critical value, a fourth control signal, in which the leaf starts to move downwards under the fourth control signal with the second critical value; and
  determining the third gain based on a difference between the first critical value and the second critical value.

9. The method of claim 5, wherein the MLC is mounted on a gantry, and the fourth gain is determined according to a process including:
  positioning the gantry at an initial angle of 0°;
  detecting a plurality of velocities of the leaf in a steady-state motion under a plurality of fourth control signals;
  generating a velocity curve illustrating a relation between the plurality of velocities and the plurality of fourth control signals; and
  designating a slope of the velocity curve as the fourth gain.

10. The method of claim 5, wherein the generating a second control signal based on at least one of a target velocity of the leaf, a target acceleration of the leaf, or a current angle of the leaf comprises:
  obtaining the current angle of the leaf; and
  generating, based on the current angle of the leaf and a fifth gain, a third component of the second control signal.

11. The method of claim 10, wherein the generating, based on the current angle of the leaf and a fifth gain, a third component of the second control signal comprises:
  generating the third component of the second control signal by multiplying a sine of the current angle of the leaf by the fifth gain.

12. The method of claim 10, wherein the MLC is mounted on a collimator, the collimator is mounted on a gantry, and the fifth gain is determined according to a process including:
  positioning the gantry at an angle of 90°;
  positioning the collimator at an initial angle of 0°;
  driving the leaf to move upwards from a stationary state by increasing, from 0 to a first critical value, a fourth control signal, in which the leaf starts to move upwards under the fourth control signal with the first critical value;
  driving the leaf to move downwards from a stationary state by increasing, from 0 to a second critical value, a fourth control signal, in which the leaf starts to move downwards under the fourth control signal with the second critical value; and
  determining the third gain based on a sum of the first critical value and the second critical value.

13. The method of claim 1, wherein the generating a first control signal based on the target position of the leaf and the current position of the leaf comprises:

determining a first difference between the target position of the leaf and the current position of the leaf;

generating an output signal of a position control loop by inputting the first difference to the position control loop;

identifying a current velocity of the leaf;

determining a second difference between the output signal of the position control loop and the current velocity of the leaf; and generating the first control signal based on the second difference and a velocity control loop.

14. The method of claim 1, wherein the identifying a current velocity of the leaf comprises:

detecting the current velocity of the leaf using a displacement sensor or an encoder.

15. The method of claim 1, wherein the identifying a current position of the leaf comprises:

detecting the current position of the leaf using a displacement sensor or an encoder.

16. The method of claim 1, wherein the MLC is mounted on a collimator, the collimator is mounted on a gantry, the method further comprising:

determining the current angle of the leaf based on a current angle of the collimator and a current angle of the gantry.

17. The method of claim 1, wherein the third control signal is a pulse width modulation (PWM) signal.

18. A system for driving a leaf of a multi-leaf collimator (MLC), comprising:

at least one storage device storing a set of instructions; and at least one processor in communication with the storage device, wherein when executing the set of instructions, the at least one processor is configured to cause the system to perform operations including:

obtaining a target position of the leaf;

identifying a current position of the leaf;

generating a first control signal based on the target position of the leaf and the current position of the leaf;

generating a second control signal based on at least one of a target velocity of the leaf, a target acceleration of the leaf, or a current angle of the leaf, wherein the second control signal is generated by a following process, including:

obtaining the target acceleration of the leaf, and generating a first component of the second control signal based on the target acceleration of the leaf and a first gain;

generating a third control signal based on the first control signal and the second control signal; and causing a drive circuit to generate a driving signal for driving the leaf to move towards the target position by providing the third control signal to the drive circuit.

19. A non-transitory computer readable medium, comprising at least one set of instructions for driving a leaf of a multi-leaf collimator (MLC), wherein when executed by one or more processors of a computing device, the at least one set of instructions causes the computing device to perform a method, the method comprising:

obtaining a target position of the leaf;

identifying a current position of the leaf;

generating a first control signal based on the target position of the leaf and the current position of the leaf;

generating a second control signal based on at least one of a target velocity of the leaf, a target acceleration of the leaf, or a current angle of the leaf, wherein the second control signal is generated by a following process, including:

obtaining the target acceleration of the leaf, and generating a first component of the second control signal based on the target acceleration of the leaf and a first gain;

generating a third control signal based on the first control signal and the second control signal; and causing a drive circuit to generate a driving signal for driving the leaf to move towards the target position by providing the third control signal to the drive circuit.

* * * * *